US010578097B2

(12) United States Patent
Cheung et al.

(10) Patent No.: US 10,578,097 B2
(45) Date of Patent: Mar. 3, 2020

(54) PERISTALTIC PUMPS AND RELATED METHODS

(71) Applicant: PerkinElmer Health Sciences, Inc., Waltham, MA (US)

(72) Inventors: Tak Shun Cheung, Toronto (CA); Chui Ha Cindy Wong, Markham (CA); Andrew Icasiano, Brampton (CA)

(73) Assignee: PerkinElmer Health Sciences, Inc., Waltham, MA (US)

( * ) Notice: Subject to any disclaimer, the term of this patent is extended or adjusted under 35 U.S.C. 154(b) by 309 days.

(21) Appl. No.: 15/481,572

(22) Filed: Apr. 7, 2017

(65) Prior Publication Data

US 2018/0171996 A1  Jun. 21, 2018

Related U.S. Application Data

(60) Provisional application No. 62/434,735, filed on Dec. 15, 2016.

(51) Int. Cl.
*F04B 43/12* (2006.01)
*A61M 5/142* (2006.01)

(52) U.S. Cl.
CPC ..... *F04B 43/1284* (2013.01); *A61M 5/14228* (2013.01); *A61M 5/14232* (2013.01); *F04B 43/1223* (2013.01); *F04B 43/1276* (2013.01)

(58) Field of Classification Search
CPC .............. F04B 43/1276; F04B 43/1284; F04B 43/1223; F04B 43/12; A61M 5/14228; A61M 5/14232
See application file for complete search history.

(56) References Cited

U.S. PATENT DOCUMENTS 3,740,173 A   6/1973  Natelson
3,999,891 A  12/1976  Galea
(Continued)

FOREIGN PATENT DOCUMENTS

JP   WO 2011118382 A1 *  9/2011  .......... F04B 43/1253

OTHER PUBLICATIONS

Machine Translation of WO 2011118382 A1 patent to Konishi, Satoshi published on Sep. 29, 2011.*

*Primary Examiner* — Peter J Bertheaud
*Assistant Examiner* — Dnyanesh G Kasture
(74) *Attorney, Agent, or Firm* — Myers Bigel, P.A.

(57) ABSTRACT

A method for pumping a fluid includes providing a peristaltic pump including a contact wall, an opposing, movable compression element, and a flexible tube interposed between the contact wall and the compression element in a compressing region. The flexible tube has a tube lengthwise axis and a through passage. The flexible tube is displaceable relative to the compressing region between a first position and a second position different from the first position. The method includes: with the flexible tube in the first position, compressing the flexible tube between the compression element and the contact wall to thereby force the fluid through the through passage; thereafter displacing the flexible tube into the second position from the first position; and thereafter, with the flexible tube in the second position, compressing the flexible tube between the compression element and the contact wall to thereby force the fluid through the through passage.

21 Claims, 12 Drawing Sheets

(56) References Cited

U.S. PATENT DOCUMENTS

| | | | |
|---|---|---|---|
| 4,131,866 A * | 12/1978 | Torr | H01F 7/1607 |
| | | | 335/255 |
| 4,178,138 A * | 12/1979 | Iles | F04B 43/1253 |
| | | | 417/360 |
| 5,533,878 A * | 7/1996 | Iwata | F04B 43/1253 |
| | | | 417/477.3 |
| 7,980,835 B2 | 7/2011 | LaBanco et al. | |
| 8,418,364 B2 | 4/2013 | McDowell et al. | |
| 8,469,682 B2 | 6/2013 | Ramirez, Jr. | |
| 2008/0095645 A1* | 4/2008 | Tam | B08B 3/026 |
| | | | 417/410.3 |
| 2015/0159642 A1* | 6/2015 | Sasa | F04B 43/1238 |
| | | | 137/544 |
| 2016/0010635 A1 | 1/2016 | Chan | |

\* cited by examiner

PERISTALTIC PUMPS AND RELATED METHODS

RELATED APPLICATIONS

The present application claims the benefit of and priority from U.S. Provisional Patent Application No. 62/434,735, filed Dec. 15, 2016, the entirety of which is incorporated by reference herein.

FIELD

The present invention relates to pumps and, more particularly, to peristaltic pumps.

BACKGROUND

Peristaltic pumps are commonly employed to displace or transfer a variety of fluids and may be particularly beneficial in pumping fluids that should be isolated from the environment. Rotary peristaltic pumps typically include two or more rollers that are driven over a length of a flexible tube such that the tube is radially pinched (e.g., against a clamp) and the fluid contents of the tube are thereby driven through the tube.

The pinched section of the tube is then permitted to relax and radially re-expand. Repeated compression and expansion of the tube can cause wear and tear in the tube. This wear and tear can result in reduced or inconsistent pump performance, and even a breach in the sidewall of the tube. Often, this degradation over time requires periodic replacement of the tube.

SUMMARY

According to embodiments of the technology, a method for pumping a fluid includes providing a peristaltic pump including a contact wall, a movable compression element, and a flexible tube. The movable compression element opposes the contact wall. The contact wall and the compression element define a compressing region therebetween. The flexible tube is interposed between the contact wall and the compression element in the compressing region. The flexible tube has a tube lengthwise axis and inner and outer opposed wall surfaces. The inner wall surface defines a through passage to receive the fluid. The flexible tube is displaceable relative to the compressing region between a first position and a second position different from the first position. The method further includes: with the flexible tube in the first position, compressing the flexible tube between the compression element and the contact wall to thereby force the fluid through the through passage; thereafter displacing the flexible tube into the second position from the first position; and thereafter, with the flexible tube in the second position, compressing the flexible tube between the compression element and the contact wall to thereby force the fluid through the through passage.

In some embodiments, the first position is a first rotational position having a first angular orientation about the tube lengthwise axis and the second position is a second rotational position having a second angular orientation about the tube lengthwise axis different from the first angular orientation, the flexible tube is rotatable about the tube lengthwise axis relative to the compressing region between the first rotational position and the second rotational position, and the step of displacing the flexible tube into the second position from the first position includes rotating the flexible tube into the second rotational position from the first rotational position.

In some embodiments, rotating the flexible tube about the tube lengthwise axis into the second rotational position includes rotating the flexible tube in a first rotation direction, and the method further includes, following the step of compressing the flexible tube between the compression element and the contact wall with the flexible tube in the second rotational position: rotating the flexible tube about the tube lengthwise axis in a second rotation direction opposite the first rotation direction into a third rotational position; and thereafter, with the flexible tube in the third rotational position, compressing the flexible tube between the compression element and the contact wall to thereby force the fluid through the through passage.

The method may include compressing the flexible tube between the compression element and the contact wall to thereby force the fluid through the through passage during the step of rotating the flexible tube about the tube lengthwise axis into the second rotational position from the first rotational position.

In some embodiments, the second angular orientation is at least 20 degrees from the first angular orientation. In some embodiments, the second angular orientation is in the range of from about 20 to 160 degrees from the first angular orientation.

According to some embodiments, the step of rotating the flexible tube about the tube lengthwise axis into the second rotational position from the first rotational position includes rotating the flexible tube using a rotator mechanism.

The rotator mechanism may include a powered actuator. In some embodiments, the rotator mechanism includes a controller that programmatically drives the actuator to rotate the flexible tube about the tube lengthwise axis.

According to some embodiments, the rotator mechanism is configured to move the compression element and/or the contact wall in a direction transverse to the tube lengthwise axis to thereby rotate the flexible tube about the tube lengthwise axis. In some embodiments, the rotator mechanism is configured to move the compression element in a first direction transverse to the tube lengthwise axis and to move the contact wall in a second direction opposite the first direction to thereby rotate the flexible tube about the tube lengthwise axis.

According to some embodiments, the first position is a first axial position and the second position is a second axial position different from the first axial position, the flexible tube is translatable along the tube lengthwise axis relative to the compressing region between the first axial position and the second axial position, and the step of displacing the flexible tube into the second position from the first position includes translating the flexible tube into the second axial position from the first axial position.

In some embodiments, translating the flexible tube along the tube lengthwise axis into the second axial position includes translating the flexible tube in a first axial direction, and the method further includes, following the step of compressing the flexible tube between the compression element and the contact wall with the flexible tube in the second axial position: translating the flexible tube along the tube lengthwise axis in a second axial direction opposite the first axial direction into a third axial position; and thereafter, with the flexible tube in the third axial position, compressing the flexible tube between the compression element and the contact wall to thereby force the fluid through the through passage.

The method may include compressing the flexible tube between the compression element and the contact wall to thereby force the fluid through the through passage during the step of translating the flexible tube along the tube lengthwise axis into the second axial position from the first axial position.

In some embodiments, the step of translating the flexible tube along the tube lengthwise axis into the second axial position from the first axial position includes axially pushing and/or pulling the flexible tube using a translator mechanism.

The translator mechanism may include a powered actuator. The translator mechanism may include a controller that programmatically drives the actuator to axially push and/or pull the flexible tube along the tube lengthwise axis.

In some embodiments, the translator mechanism includes a spool, and the step of translating the flexible tube along the tube lengthwise axis includes forcibly winding the flexible tube onto the spool.

In some embodiments, the translator mechanism further includes a second spool, and the step of translating the flexible tube along the tube lengthwise axis includes unwinding the flexible tube from the second spool.

In some embodiments, the step of translating the flexible tube along the tube lengthwise axis further includes unwinding the flexible tube from the spool.

In some embodiments, the step of compressing the flexible tube between the compression element and the contact wall with the flexible tube in the second position includes forcing the compression element to travel down a length of the flexible tube while engaging and compressing the flexible tube to thereby push the fluid axially through the through passage.

In some embodiments, the peristaltic pump is a rotary peristaltic pump and the compression element is a compression roller, shoe or wiper.

The rotary peristaltic pump may include a rotor and a plurality of circumferentially spaced apart compression rollers, shoes or wipers located on the rotor for rotation therewith. The step of compressing the flexible tube between the compression element and the contact wall with the flexible tube in the second position includes compressing the flexible tube between the contact wall and each of the compression rollers, shoes or wipers.

The peristaltic pump may be a linear peristaltic pump including a plurality of movable compression elements arranged in series.

According to embodiments of the technology, a peristaltic pump for pumping a fluid includes a contact wall, a movable compression element, a flexible tube, and a tube displacement mechanism. The movable compression element opposes the contact wall. The contact wall and the compression element define a compressing region therebetween. The flexible tube is interposed between the contact wall and the compression element in the compressing region. The flexible tube has a tube lengthwise axis and inner and outer opposed wall surfaces. The inner wall surface defines a through passage to receive the fluid. The tube displacement mechanism is operable to displace the flexible tube relative to the compressing region between a first position and a second position different from the first position. The peristaltic pump is configured to compress the flexible tube between the compression element and the contact wall to thereby force the fluid through the through passage with the flexible tube in each of the first and second positions.

In some embodiments, the first position is a first rotational position having a first angular orientation about the tube lengthwise axis and the second position is a second rotational position having a second angular orientation about the tube lengthwise axis different from the first angular orientation, and the tube displacement mechanism is a rotator mechanism operable to rotate the flexible tube about the tube lengthwise axis relative to the compressing region between the first rotational position and the second rotational position.

The rotator mechanism may be operable to rotate the flexible tube about the tube lengthwise axis from the first rotational position to the second rotational position in a first rotation direction, and rotate the flexible tube about the tube lengthwise axis from the second rotational position to a third rotational position in a second rotation direction opposite the first rotation direction.

According to some embodiments, the peristaltic pump is configured to compress the flexible tube between the compression element and the contact wall to thereby force the fluid through the through passage while the rotator mechanism is rotating the flexible tube about the tube lengthwise axis into the second rotational position from the first rotational position.

In some embodiments, the second angular orientation is at least 20 degrees from the first angular orientation. In some embodiments, the second angular orientation is in the range of from about 20 to 160 degrees from the first angular orientation.

The rotator mechanism may include a powered actuator. The rotator mechanism may include a controller that programmatically drives the actuator to rotate the flexible tube about the tube lengthwise axis.

The rotator mechanism may be configured to move the compression element and/or the contact wall in a direction transverse to the tube lengthwise axis to thereby rotate the flexible tube about the tube lengthwise axis. The rotator mechanism may be configured to move the compression element in a first direction transverse to the tube lengthwise axis and to move the contact wall in a second direction opposite the first direction to thereby rotate the flexible tube about the tube lengthwise axis.

In some embodiments, the first position is a first axial position and the second position is a second axial position different from the first axial position, and the tube displacement mechanism is a translator mechanism operable to translate the flexible tube along the tube lengthwise axis relative to the compressing region between the first axial position and the second axial position.

The translator mechanism may be operable to: translate the flexible tube along the tube lengthwise axis from the first axial position to the second axial position in a first displacement direction; and translate the flexible tube along the tube lengthwise axis from the second axial position to a third axial position in a second displacement direction opposite the first displacement direction.

According to some embodiments, the peristaltic pump is configured to compress the flexible tube between the compression element and the contact wall to thereby force the fluid through the through passage while the translator mechanism is translating the flexible tube along the tube lengthwise axis into the second axial position from the first axial position.

The translator mechanism may include a powered actuator. In some embodiments, the translator mechanism includes a controller that programmatically drives the actuator to translate the flexible tube along the tube lengthwise axis.

In some embodiments, the translator mechanism includes a spool, and the translator mechanism is operable to forcibly wind the flexible tube onto the spool to translate the flexible tube along the tube lengthwise axis.

In some embodiments, the translator mechanism further includes a second spool, and the translator mechanism is operable to unwind the flexible tube from the second spool to translate the flexible tube along the tube lengthwise axis.

In some embodiments, the translator mechanism is further operative to unwind the flexible tube from the spool to translate the flexible tube along the tube lengthwise axis.

The peristaltic pump may be configured to compress the flexible tube between the compression element and the contact wall with the flexible tube in the second axial position by forcing the compression element to travel down a length of the flexible tube while engaging and compressing the flexible tube to thereby push the fluid axially through the through passage.

In some embodiments, the peristaltic pump is a rotary peristaltic pump and the compression element is a compression roller, shoe or wiper.

According to some embodiments, the rotary peristaltic pump includes a rotor and a plurality of circumferentially spaced apart compression rollers, shoes or wipers located on the rotor for rotation therewith. The peristaltic pump is configured to compress the flexible tube between the contact wall and each of the compression rollers, shoes or wipers.

According to some embodiments, the peristaltic pump is a linear peristaltic pump including a plurality of movable compression elements arranged in series.

Further features, advantages and details of the present technology will be appreciated by those of ordinary skill in the art from a reading of the figures and the detailed description of the preferred embodiments that follow, such description being merely illustrative of the present technology.

DETAILED DESCRIPTION

Figure 1:
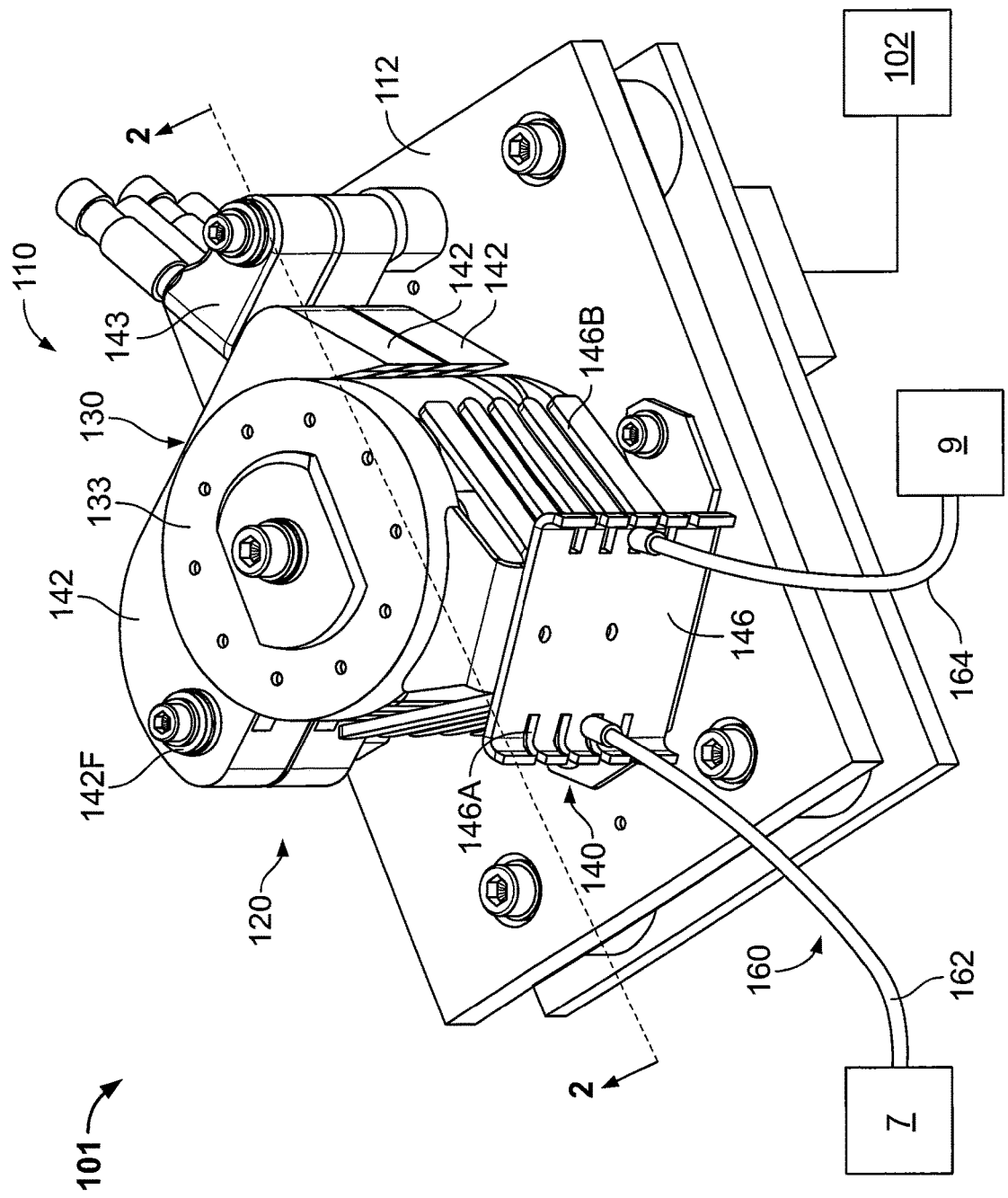
FIG. 1 is a top perspective view of a fluid management system according to embodiments of the technology, the fluid management system including a pump assembly.

The present technology now will be described more fully hereinafter with reference to the accompanying drawings, in which illustrative embodiments of the technology are shown. In the drawings, the relative sizes of regions or features may be exaggerated for clarity. This technology may, however, be embodied in many different forms and should not be construed as limited to the embodiments set forth herein; rather, these embodiments are provided so that this disclosure will be thorough and complete, and will fully convey the scope of the technology to those skilled in the art.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present technology.

Spatially relative terms, such as "beneath", "below", "lower", "above", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90° or at other orientations) and the spatially relative descriptors used herein interpreted accordingly.

As used herein, the singular forms "a", "an" and "the" are intended to include the plural forms as well, unless expressly stated otherwise. It will be further understood that the terms "includes," "comprises," "including" and/or "comprising," when used in this specification, specify the presence of stated features, integers, steps, operations, elements, and/or components, but do not preclude the presence or addition of one or more other features, integers, steps, operations, elements, components, and/or groups thereof. It will be understood that when an element is referred to as being "connected" or "coupled" to another element, it can be directly connected or coupled to the other element or intervening elements may be present. As used herein, the term "and/or" includes any and all combinations of one or more of the associated listed items.

Unless otherwise defined, all terms (including technical and scientific terms) used herein have the same meaning as commonly understood by one of ordinary skill in the art to which this technology belongs. It will be further understood that terms, such as those defined in commonly used dictionaries, should be interpreted as having a meaning that is consistent with their meaning in the context of this specification and the relevant art and will not be interpreted in an idealized or overly formal sense unless expressly so defined herein.

The term "monolithic" means an object that is a single, unitary piece formed or composed of a material without joints or seams.

The term "automatically" means that the operation is substantially, and may be entirely, carried out without human or manual input, and can be programmatically directed or carried out.

The term "programmatically" refers to operations directed and/or primarily carried out electronically by computer program modules, code and/or instructions.

Embodiments of the technology are directed to reducing the problems associated with peristaltic pumps as described above. According to method embodiments of the technology, a peristaltic pump is provided including one or more compression elements and an opposing contact wall. The compression element(s) and the contact wall define a compressing region therebetween. A flexible tube is interposed between the contact wall and the compression element(s) in the compressing region. The flexible tube has a tube lengthwise axis and inner and outer opposed wall surfaces. The inner wall surface defines a through passage to receive the fluid. The flexible tube is displaceable relative to the compressing region between a first position and a second position different from the first position. The peristaltic pump is configured such that, when operated, the compression element(s) and the contact wall cooperatively apply a pressure or compressive load to the portion of flexible tube in the compressing region. This compressive load radially compresses, collapses and deforms the tube in the compressing region. The compressive load may be substantially perpendicular to the tube lengthwise axis at the axial location where the compressive load is applied.

With the flexible tube in the first position, the flexible tube is compressed between the compression element(s) and the contact wall to thereby force the fluid through the through passage. Thereafter, the flexible tube is displaced into the second position from the first position. Thereafter, with the flexible tube in the second position, the flexible tube is compressed between the compression element and the contact wall to thereby force the fluid through the through passage. In practice, the flexible tube will typically be cyclically compressed in the compressing region by the compression elements many times in each of (and, in some cases, between) the first and second positions.

By relatively repositioning the flexible tube and the compressing region (i.e., the spatial region with respect to the compression element(s) and the contact wall in which the compressive load is applied), deformation of the tube caused by the compressive load of the compression element(s) is more widely distributed across the tube. Localized wear and tear, aging, and degradation of the tube can be reduced. Beneficially, this can prolong the effective service life of the tube and improve the performance of the tube during use.

In some embodiments, the flexible tube is rotated about its lengthwise axis to reposition the tube relative to the compressing region. In this case, the angular orientation of the tube relative to the compressing region is changed, thereby changing the direction or angle of the compressive load with respect to the tube (e.g., in a plane orthogonal to the tube lengthwise axis). Thus, the axial section of the tube may remain in the compressing region, but the shape of deformation of the tube (in particular, the circumferential locations of opposed bends in the tube) is varied.

In some embodiments, the flexible tube is axially displaced or translated (e.g., axially pulled or pushed) along its lengthwise axis relative to the compressing region. In this case, the tube section originally in the compressing region is replaced with a new, different lengthwise section of the tube in the compressing region. Thus, the angular orientation of the tube may remain the same, but the axial section of the tube to which the compressive load is applied and that is deformed is changed.

In some embodiments, both the angular orientation and the relative axial position of the tube with respect to the compressing region are changed.

With reference to FIGS. 1-7C, a fluid management system 101 according to embodiments of the technology is shown therein. The fluid management system 101 (FIG. 1) includes a pump assembly 110 according to embodiments of the technology, a controller 102, a supply 7 of a fluid 5, and a receiver 9.

The supply 7, the fluid 5 and the receiver 9 may be any suitable supply, fluid and receiver. The supply 7 may be a container containing a quantity of the fluid 5 and from which the fluid 5 is to be drawn, for example. The receiver 9 may be a container or further processing station to which the fluid 5 is to be delivered or dispensed. The fluid 5 may be a liquid and/or a gas.

The pump assembly 110 includes a chassis or base 112, a rotor drive system 114, a rotator mechanism 150, and a pump mechanism 120. It will be appreciated that the pump assembly 110 can be used in combination with supports and drive systems of other designs and constructions.

Figure 2:
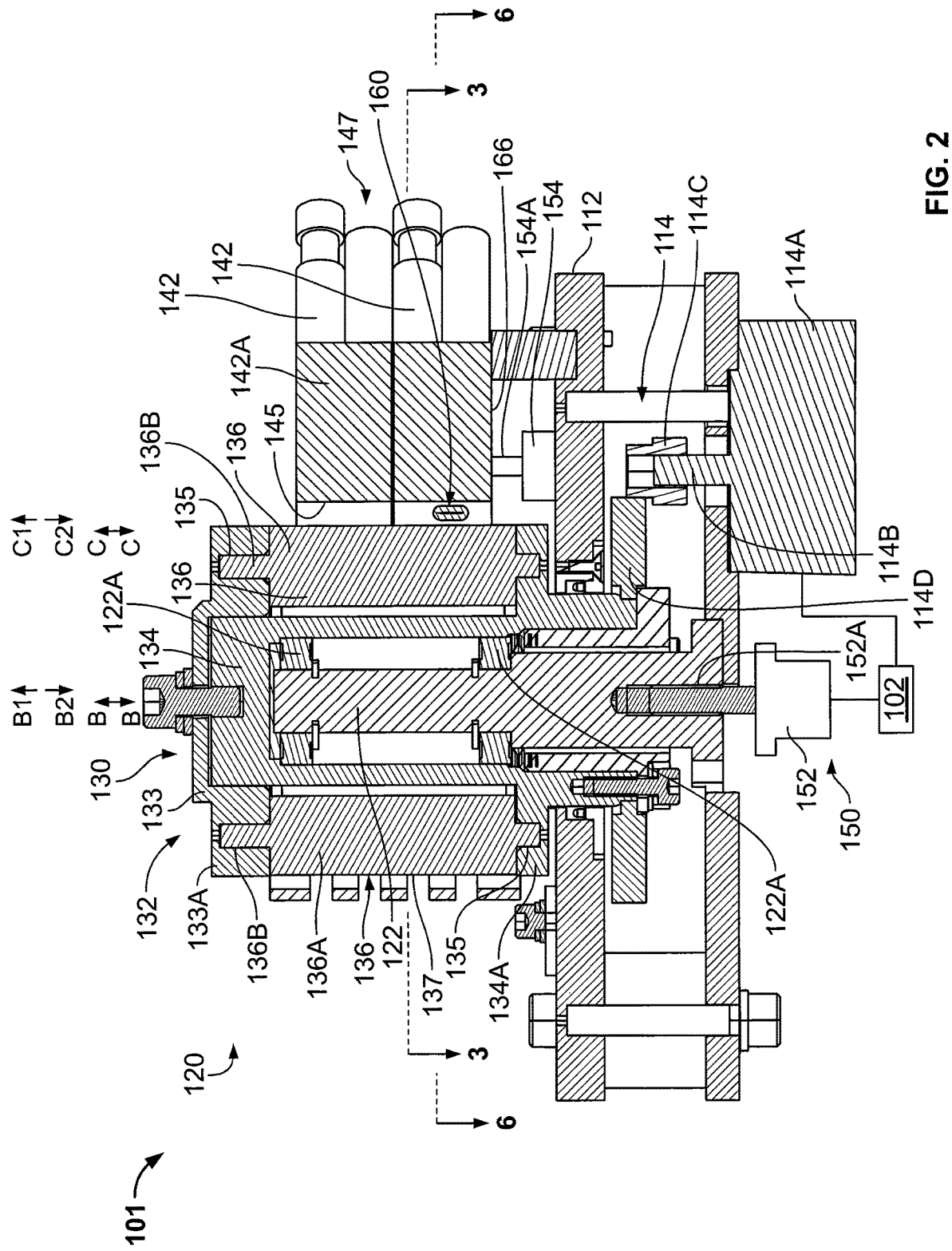
FIG. 2 is a fragmentary, cross-sectional view of the fluid management system of FIG. 1 taken along the line 2-2 of FIG. 1.

With reference to FIG. 2, the rotor drive system 114 includes a motor 114A having a rotatable output shaft 114B. The motor 114A may be any suitable motor and, in some embodiments, is an electric motor configured to be selectively actuated and deactuated by the controller 102. A drive gear 114C is affixed to the output shaft 114B for rotation therewith.

The pump mechanism 120 includes a primary axle 122, a pump housing or casing 140, one or more elastically deformable or flexible tubes 160, and a rotor assembly 130.

The primary axle 122 is affixed at its base to the base 112 and has bearings 122A mounted on its upper and mid sections. The bearings 122A may be roller bearings, for example.

The pump housing 140 includes a plurality of rigid, semi-circular clamps 142 and a fixed housing section or shroud 146 collectively defining a pump chamber 141. Each clamp 142 includes a clamp body 142A, an arcuate, inner contact wall 145, and a pivot end 142D. Each clamp 142 is pivotally coupled to the base 112 by a pivot bolt 142F at its pivot end 142D and releasably secured in a closed position adjacent the rotor assembly 130 by a locking mechanism 143 at its opposing end 142E. Slots 146A, 146B are defined in the shroud 146 and generally align with the grooves 142C. The shroud 146 is affixed to the base 112 by bolts, for example. The clamps 142 and locking mechanism 143 collectively form a clamp unit 147 that can be extended and retracted with respect to the base 112, as discussed below.

The clamps 142 and their contact walls 145 may be formed of any suitable material(s). Suitable materials may include, for example, stainless steel or polyphenylene sulfide. Typically, the clamps 142 will be hard and the contact walls 145 will be relatively smooth.

The rotor assembly 130 (FIGS. 1 and 2) includes a roller carrier 132 and a plurality of rollers 136 circumferentially distributed about the carrier 132.

The roller carrier 132 includes a hub 134 and an end cap 133 coupled by a bolt. The hub 134 includes a radially outwardly extending lower flange 134A. The end cap 133 includes a radially outwardly extending upper flange 133A. The flanges 134A and 133A define an annular roller receiving channel therebetween. A driven gear 114D is affixed to the lower end of the hub 134 and operably engages the drive gear 114C to be driven thereby. Roller mounting bores 135 are defined in each flange 134A, 133A for each roller 136.

Figure 6:
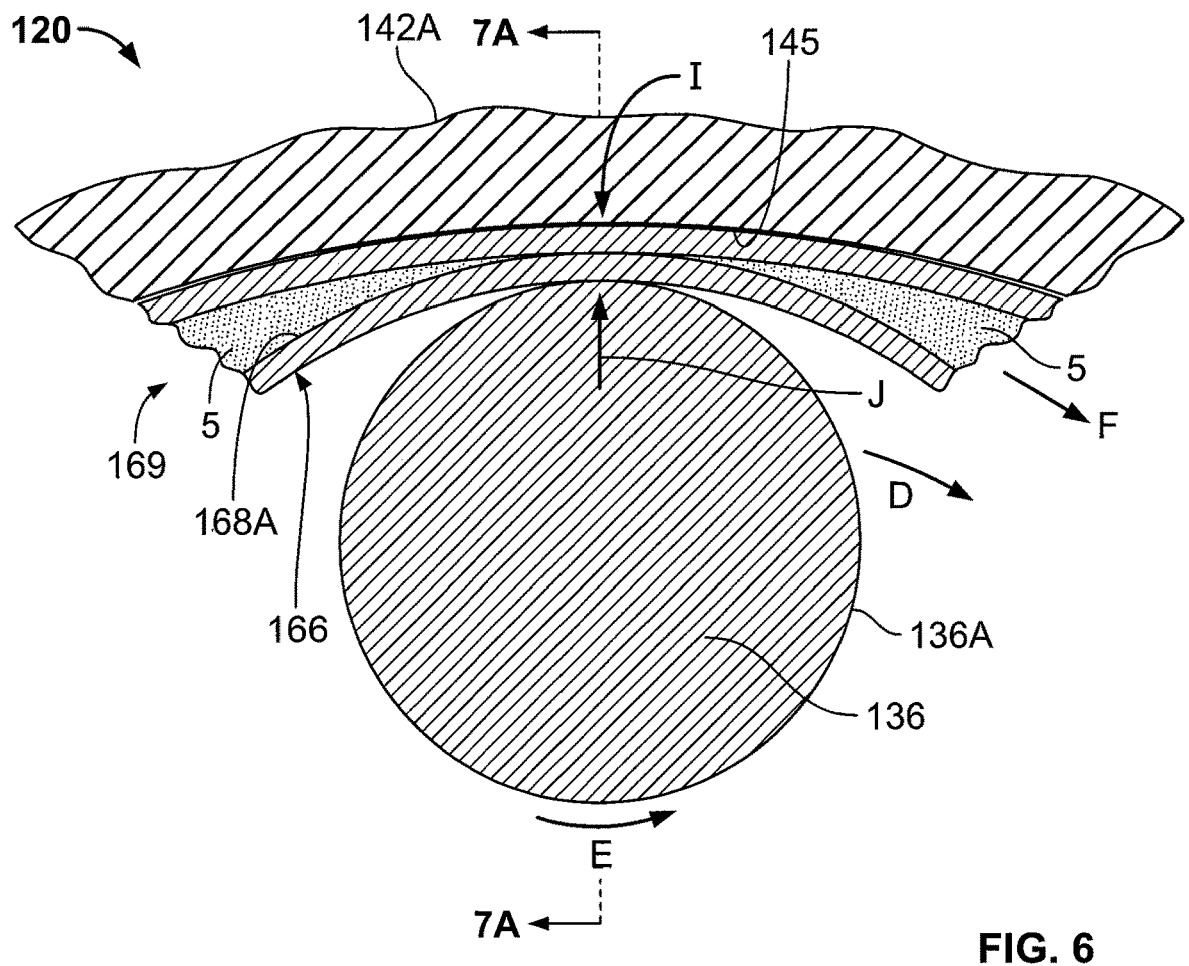
FIG. 6 is an enlarged, fragmentary, cross-sectional view of the pump assembly of FIG. 1 taken along the line 6-6 of FIG. 2.

With reference to FIGS. 2 and 6, each roller 136 includes a tubular body 136A and a pair of integral, opposed axle pin features 136B extending axially from either end of the body 136A. Each tubular body 136A has an outer contact surface 137. According to some embodiments, each contact surface 137 is cylindrical.

The opposed axle pins 136B are rotatably seated in opposed roller mounting bores 135. The rollers 136 and rotor 130 may be otherwise constructed to permit rotation of the rollers 136. For example, the rollers 136 may be mounted on a separate axle pin or axle features integral with the hub 134 and end cap 133, for example. According to some embodiments, the rollers 136 are evenly spaced apart circumferentially about the hub 134.

The rollers 136 and their contact surfaces 137 may be formed of any suitable material(s). Suitable materials may include, for example, metal (e.g., stainless steel) or polyphenylene sulfide. Typically, the rollers 136 will be hard and the contact surfaces 137 will be relatively smooth.

The pump mechanism 120 may include multiple tubes 160. However, only one tube 160 is shown in the drawings and will be described in detail below. The description of the flexible tube 160 likewise applies to the other tubes.

According to some embodiments and as shown, the flexible tube 160 is substantially circular in cross-section. The flexible tube 160 includes an inlet section 162, an outlet section 164, and an intermediate or active section 166. The tube 160 defines a through passage 169 extending continuously from an inlet to an outlet. The tube 160 has an inner surface 168A (defining the through bore 169) and an outer surface 168B. The tubes 160 may be formed of any suitable flexible, resilient material or materials. According to some embodiments, the tube 160 is formed of a resilient polymeric material. Suitable materials may include polyvinyl chloride (PVC) or TYGON™ tubing, for example. In some embodiments, the tube 160 is formed of a material having a hardness in the range of from about Shore A 40 to Shore A 70.

Figure 3:
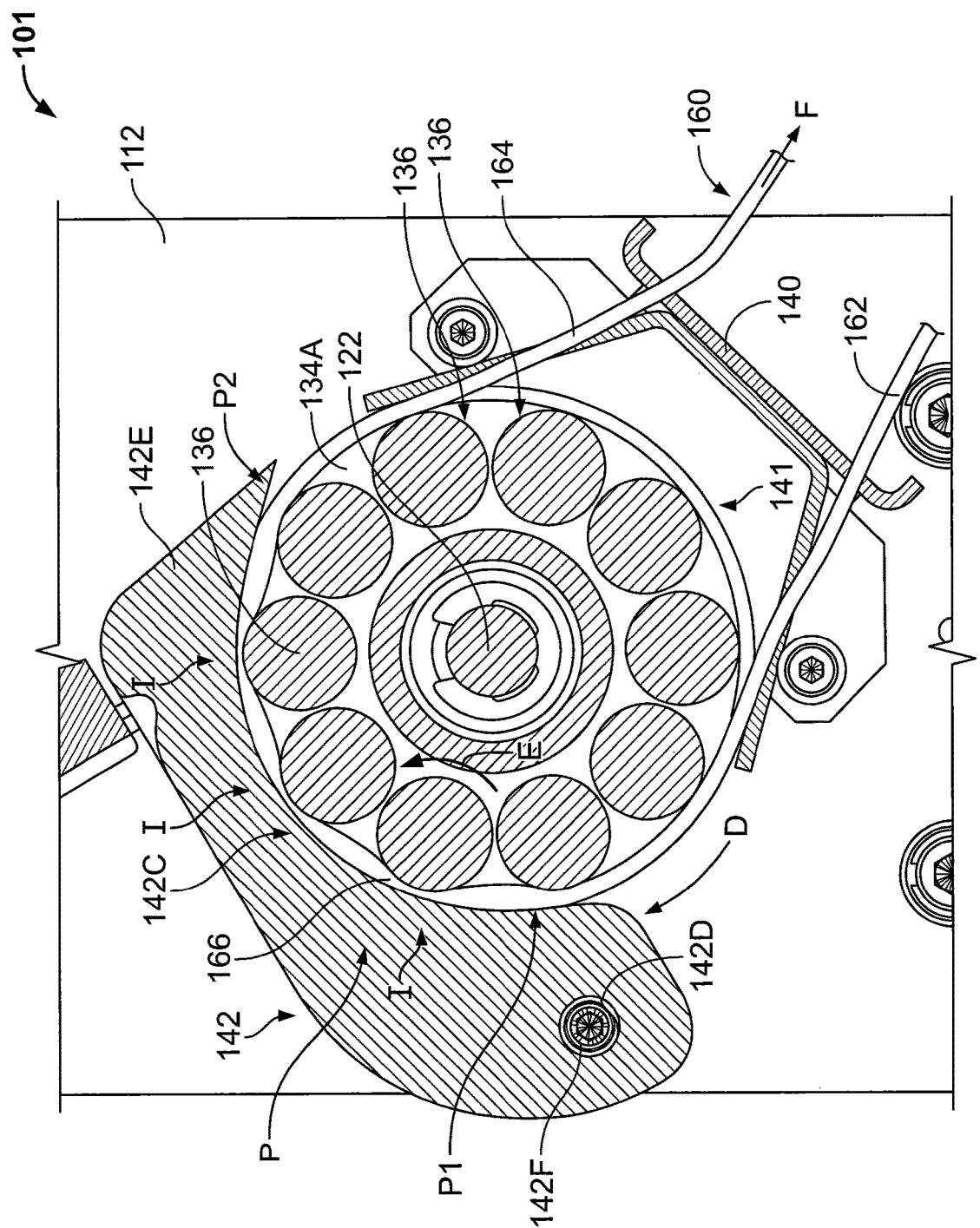
FIG. 3 is a cross-sectional view of the fluid management system of FIG. 1 taken along the line 3-3 of FIG. 2.
Figure 4:
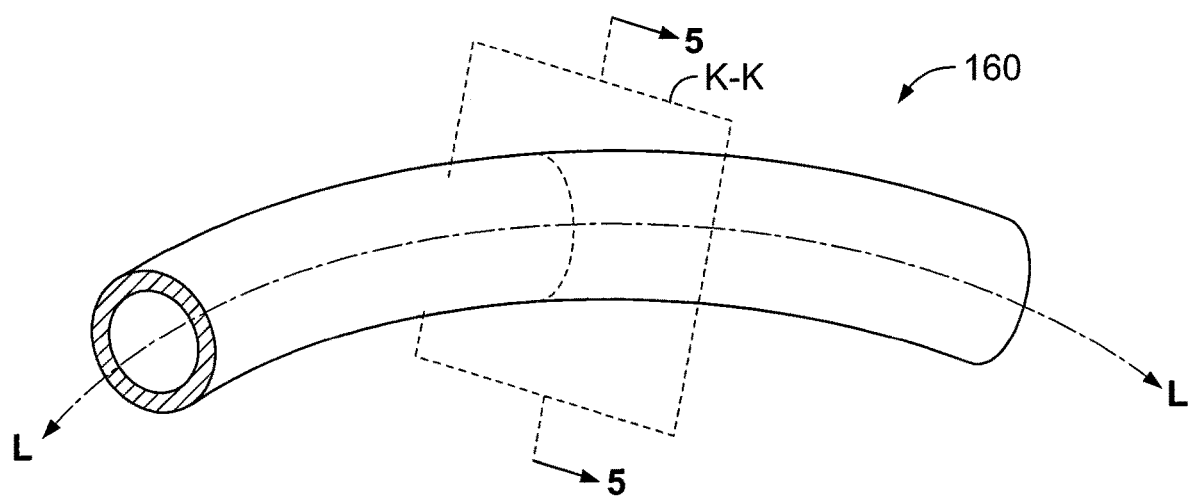
FIG. 4 is a fragmentary, perspective view of a section of flexible tube forming a part of the fluid management system of FIG. 1.

The tube 160 has a central tube longitudinal axis L-L. The tube longitudinal axis L-L is centered in the through passage 169 and extends the length of the tube 160. It will be appreciated that when the tube 160 is bent or curved (e.g., as shown in FIGS. 3, 4 and 6), the longitudinal axis L-L is correspondingly curved.

Reference is made herein to the angular orientation of the tube 160 about the longitudinal axis L-L. At any given location or point along the axis L-L, the angular orientation of the tube 160 can be observed in a cross-sectional reference plane K-K (FIGS. 4 and 5) extending orthogonally to the longitudinal axis L-L at that point along the axis L-L.

The rotator mechanism 150 includes a roller repositioning actuator 152 having an output shaft 152A connected to the hub 134. The roller repositioning actuator 152 is operable to drive (i.e., push and pull) the hub 134 in opposing roller displacement directions B1 and B2 (FIGS. 2, 7A and 7B) along the axis B-B relative to the clamp unit 147.

The rotator mechanism 150 further includes a contact wall repositioning actuator 154 having an output shaft 154A connected to the clamp unit 147. The contact wall repositioning actuator 154 is operable to drive (i.e., push and pull) the clamp unit 147 in opposing contact wall displacement directions C1 and C2 (FIGS. 2, 7A and 7B) along an axis C-C relative to the rollers 136.

The actuators 152, 154 may be electrically connected to and controlled by the controller 102. The actuators 152, 154 may be any suitable type or types of actuator(s). Suitable actuators may include a solenoid or electric stepper motor with or without a linkage between the output of the actuator and the hub 134 or clamp unit 147.

The rotor assembly 130 is mounted over the primary axle 122 on the bearings 122A for rotation about a central rotation axis B-B. The rotor assembly 130 may be secured in place by a locking collar. The tubes 160 (only one shown) are looped about the rotor assembly 130 and the central rotation axis B-B as shown in FIG. 3. More particularly, the intermediate section 166 of each tube 160 extends around the outer diameter of the rotor assembly 130 between the rotor assembly 130 and a respective clamp 142 such that the tube intermediate section 166 is seated in the gap between the rollers 136 and the clamp contact wall 145. The tube sections 166 and the rotor assembly 130 are thus both disposed in the pump chamber 141. The inlet section 162 of the tube 160 is fluidly connected to the supply 7 and the outlet section 164B is fluidly connected to the receiver 9.

In operation, one or more of the tubes 160 may be used to pump the fluid 5. For the purpose of explanation, only a single tube 160 will be described below and is shown in the figures. It will be appreciated, however, that this discussion likewise applies to operation using other tubes 160, individually or simultaneously, that are mounted against respective other ones of the clamps 142.

With the tube 160 looped about the rotor assembly 130, the clamp 142 is closed and locked to the shroud 146 using the locking mechanism 143 to capture and compress the tube section 166 between the clamp 142 and the rotor assembly 130. The clamp contact wall 145 and the roller contact surfaces 137 cooperatively define a compressing region P (FIG. 3) radially therebetween. The compressing region P is arcuate and extends circumferentially from the location P1 along the contact wall 145 where a roller 136 can first compress the tube section 166 to the location P2 along the contact wall 145 where the roller 136 can last compress the tube section 166 as the roller rotates fully across the clamp 142.

The controller 102 operates the motor 114A to drive the rotor assembly 130 to rotate in a circular direction D about the central axis B-B. The spacing between each roller contact surface 136A and the clamp contact wall 145 when they are circumferentially adjacent is less than the outer diameter of the relaxed tube 160 in the compressing region P. As the rotor assembly 130 rotates, the rollers 136 orbit the central axis B-B. The rollers 136 in contact with the tube section 166 rotate (in a direction E (FIGS. 3 and 6)) about the roller axis over the intermediate section 166 and thereby sequentially locally radially compress or pinch the intermediate section 166 in a pinched direction J (FIG. 6) against the clamp wall 145 at moving pinch locations I throughout the compressing region P. At each pinch location I, the tube 160 is collapsed, deformed or flattened to form substantially flat or elongate side sections 170 connected by opposed bends or folds 172, as shown in the cross-sectional view of FIG. 7A. The rollers 136 thereby operate as pressing or compression elements while the clamp wall 145 serves as an occlusion bed. In some embodiments, the rollers 136 fully occlude the through passage 169 at the pinched locations I (FIGS. 3 and 6). In some embodiments, the rollers 136 do not fully occlude the through passage 169.

As the rotor assembly 130 is rotated, the pinched point or location I of each contacting roller 136 moves or translates progressively down the length of the tube 160 toward the outlet section 164. In this manner, the fluid 5 in the through bore 169 is squeezed or pushed ahead of the rollers 136 in a fluid flow or displacement direction F (FIG. 3) through the through passage 169 along the longitudinal axis of the tube 160. The pump mechanism 120 thereby operates as a positive displacement pump. After the roller 136 passes over the section 166 of the tube 160, the tube section 166 will resiliently or elastically return (restitution) to its original relaxed or radially expanded state, thereby inducing or drawing more fluid 5 from the supply 7 into through bore 169. This additional fluid 5 is pushed through the through bore 169 by the next revolution of the rotor assembly 130. The fluid 5 exits the pump mechanism 120 through the tube outlet section 164.

Over time, the repeated compression and restitution of the tube 160 may cause the tube section 166 to lose its resilience, which may in turn reduce the consistency and/or efficiency of the pump mechanism 120. The repeated compression and restitution of the tube section 166 may also eventually cause the tube section 166 to break, rupture, or fail and permit the fluid 5 to leak out from the tube section 166 into the surrounding regions of the pump mechanism (e.g., into the pump chamber 141). For example, pin holes, slits or splits may form in the tube section 166 through which the fluid 5 may leak.

The foregoing problems may be solved or reduced by the rotator mechanism 150. In use, the rotator mechanism 150 forcibly rotates the tube section 166 about its lengthwise axis L-L relative to the rollers 136 and the contact wall 145 to thereby change the angular orientation of the tube section 166 about the lengthwise axis L-L in the active section 166 relative to the compressing region P. The rotator mechanism 150 may be controlled to rotate the tube section 166 in this manner while the fluid is being pumped (i.e., while the rotor 130 is rotating). Alternatively, or additionally, the rotator mechanism 150 may be controlled to rotate the tube section 166 between pumping sessions (i.e., the rotor 130 is rotated and stopped, the tube section 166 is then rotated about the lengthwise axis L-L, and the rotor 130 is then rotated again). As a result, the locations of the bends 172 on the tube section 166 are relocated about the circumference of the tube section 166. In this manner, the small or sharp radius bends 172 are more widely distributed around the circumference of the tube, thereby reducing the amount of repetitive deformation experienced by any one location for a given duration of pumping.

Figure 5:
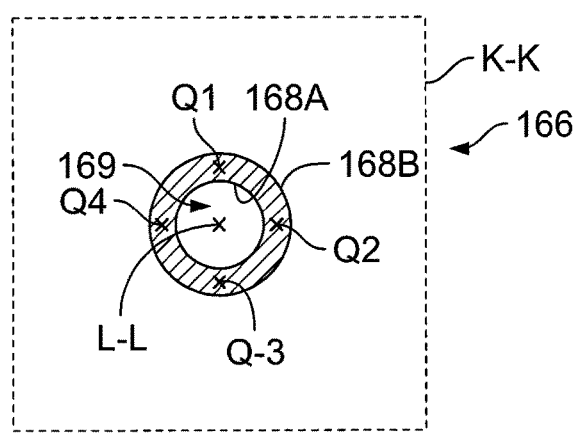
FIG. 5 is a cross-sectional view of the flexible tube of FIG. 4 taken along the line 5-5 of FIG. 4.

The rotation of the tube section 166 will be further described with reference to FIGS. 4-7C, wherein a cross-section of the tube section 166 is shown in a reference cross-sectional plane K-K that is orthogonal to the lengthwise axis L-L. FIGS. 4 and 5 show the tube section 166 in its relaxed, noncompressed state. FIGS. 6-7C show the tube section 166 at a pinch location I in its compressed state.

Figure 7A:
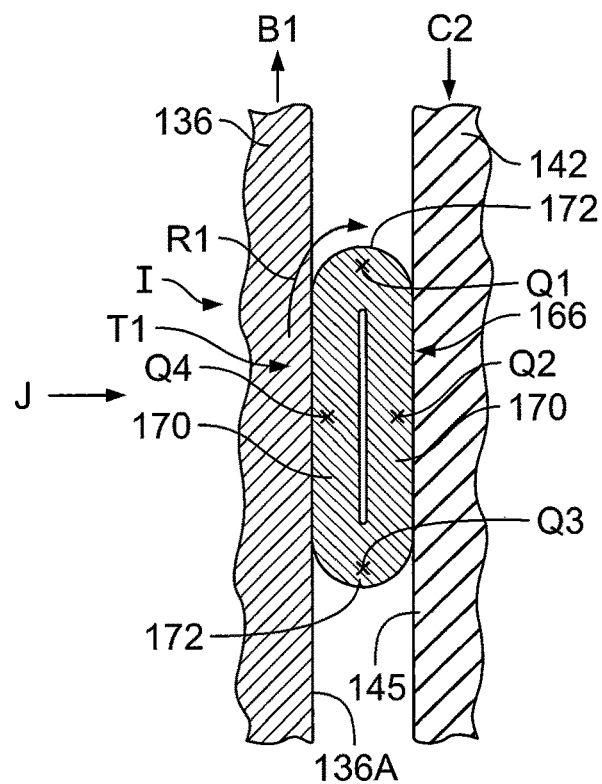
FIGS. 7A-7C are fragmentary, cross-sectional views of the pump assembly of FIG. 2 taken along the line 7A-7A of FIG. 6 illustrating a sequence of rotation of the flexible tube of FIG. 1.
Figure 7C:
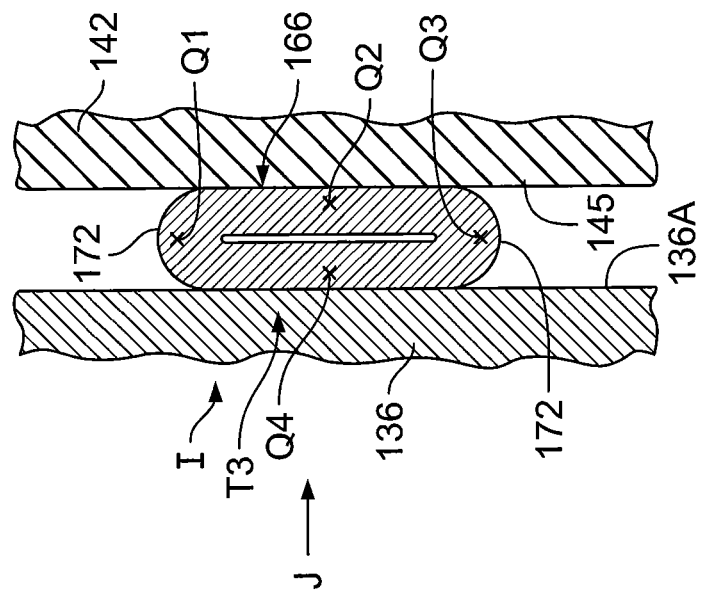

FIG. 7A shows the compressed tube section 166 in its initial angular orientation T1 in a first rotational position. Circumferential reference points Q1-Q4 are labeled in FIG. 7A-7C for the purpose of explanation. As shown in FIG. 7A, in the first rotational position the reference point Q1 is located at the center of the upper tube fold 172.

Figure 7B:
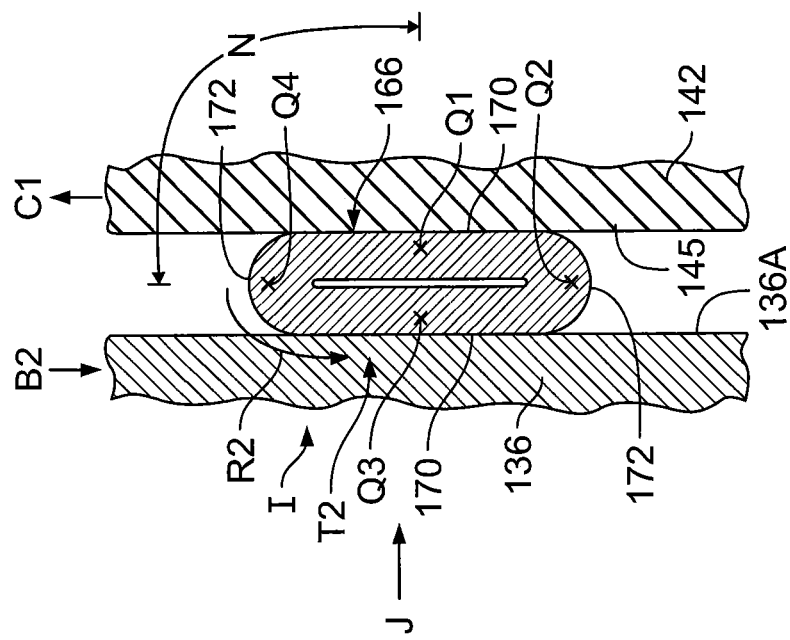

With the tube section 166 in the first rotational position (FIG. 7A), the controller 102 operates the rotator mechanism 150 to rotate the tube section 166 in a first rotation direction R1 into a second rotational position as shown in FIG. 7B wherein the tube section 166 has a second angular orientation T2 different from the first angular orientation T1. More particularly, the roller repositioning actuator 152 drives the hub 134, and thereby the roller contact surface 137, in the extension direction B1 relative to the contact wall 145 and the tube section 166. The contact wall repositioning actuator 154 drives the clamp unit 147, and thereby the contact wall 145, in the retraction direction C2 relative to the roller contact surface 137 and the tube section 166. The movements of the contact surfaces 137, 145 force the tube section 166 to rotate in the first direction R1. In some embodiments, the roller repositioning actuator 152 and the contact wall repositioning actuator 154 are operated simultaneously. In some embodiments, the roller repositioning actuator 152 and the contact wall repositioning actuator 154 are sequentially operated.

It will be appreciated that when the tube section 166 is in the second angular orientation T2, the axis or direction J (FIGS. 6-7C) of the compressive load applied by the roller contact surface 137 intersects the tube 160 at a different circumferential location than when the tube section 166 is in the first angular orientation T1.

According to some embodiments, the angular displacement N (FIG. 7B) between the first angular orientation T1 and the second angular orientation T2 is at least 20 degrees, in some embodiments, is in the range of from about 20 to 160 degrees and, in some embodiments, is substantially 90 degrees.

In accordance with some embodiments, with the tube section 166 in the second rotational position (FIG. 7B), the controller 102 operates the rotator mechanism 150 to rotate the tube section 166 in a second rotation direction R2 into a third rotational position as shown in FIG. 7C. More particularly, the roller repositioning actuator 152 drives the hub 134, and thereby the roller contact surface 137, in the retraction direction B2 relative to the contact wall 145 and the tube section 166. The contact wall repositioning actuator 154 drives the clamp unit 147, and thereby the contact wall 145, in the extension direction C1 relative to the roller contact surface 137 and the tube section 166. The movements of the contact surfaces 137, 145 force the tube section 166 to rotate in the second direction R2. In some embodiments, the roller repositioning actuator 152 and the contact wall repositioning actuator 154 are operated simultaneously. In some embodiments, the roller repositioning actuator 152 and the contact wall repositioning actuator 154 are sequentially operated.

In some embodiments and as shown in FIG. 7C, the third rotational position is the same as the first rotational position (FIG. 7A) and the angular orientation of the tube section 166 in the third rotational position is substantially the same as the first angular orientation T1. However, in other embodiments, the angular orientation of the tube section 166 in the third rotational position is greater or less than the first angular orientation T1.

The foregoing process may be executed only once or multiple times with the same tube section 166. If executed multiple times, the process may be executed continuously or periodically. The tube section 166 may be rotated during or between pumping cycles. In some embodiments, the rotation from the first rotation position to the second rotational position is executed while the pump mechanism 120 is pumping. In some embodiments, the rotation from the second rotation position to the third rotational position is executed while the pump mechanism 120 is pumping. In some embodiments, the both rotations are executed while the pump mechanism 120 is pumping.

In some embodiments, the controller 102 automatically and programmatically operates the motor 114A, the roller repositioning actuator 152, and the contact wall repositioning actuator 154 to execute the actions, processes and steps discussed above. In other embodiments or modes, the roller repositioning actuator 152 and the contact wall repositioning actuator 154 are manually operated.

Figure 8:
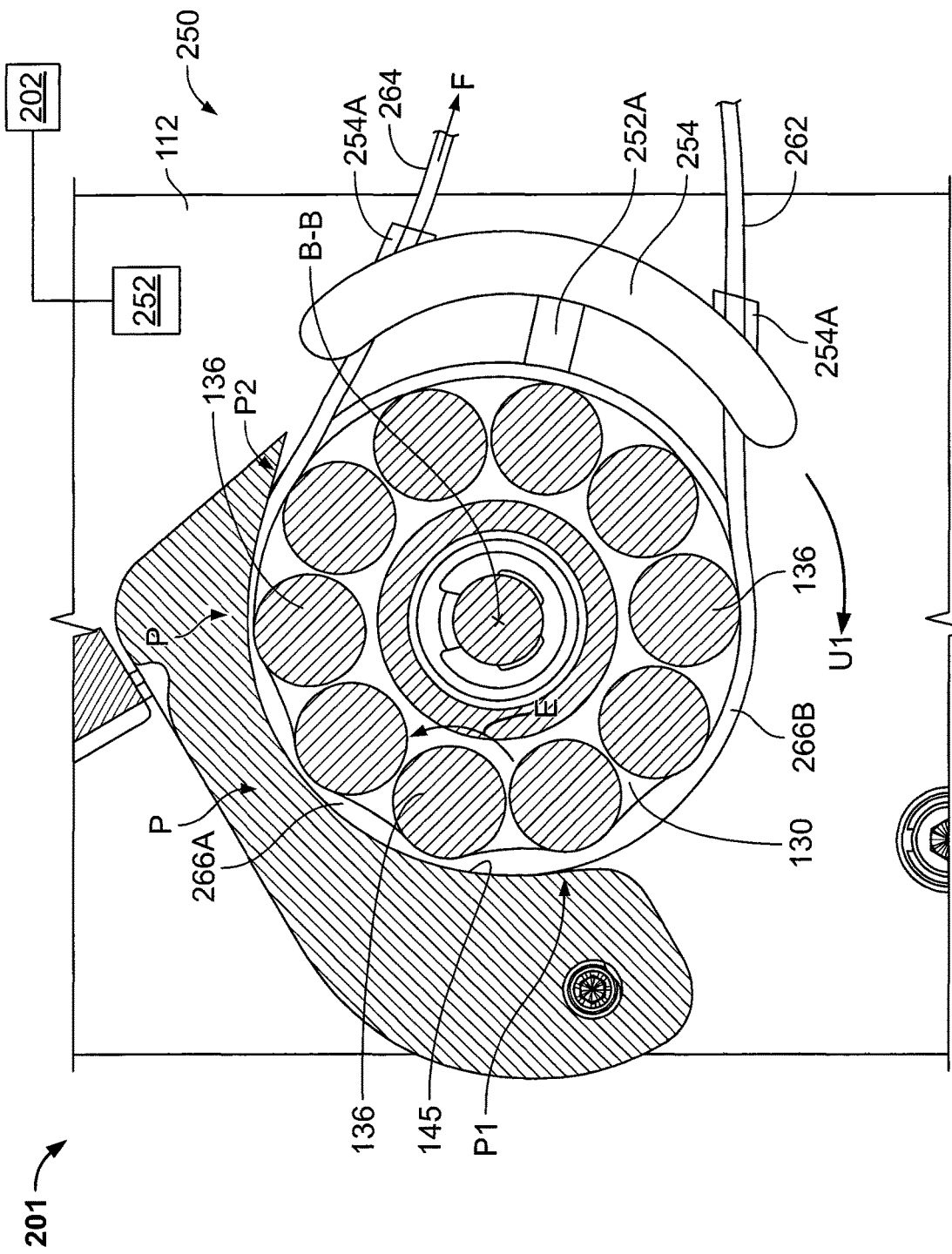
FIG. 8 is a fragmentary, cross-sectional view of a fluid management system according further embodiments of the technology with a rotator mechanism thereof in a first position.
Figure 9:
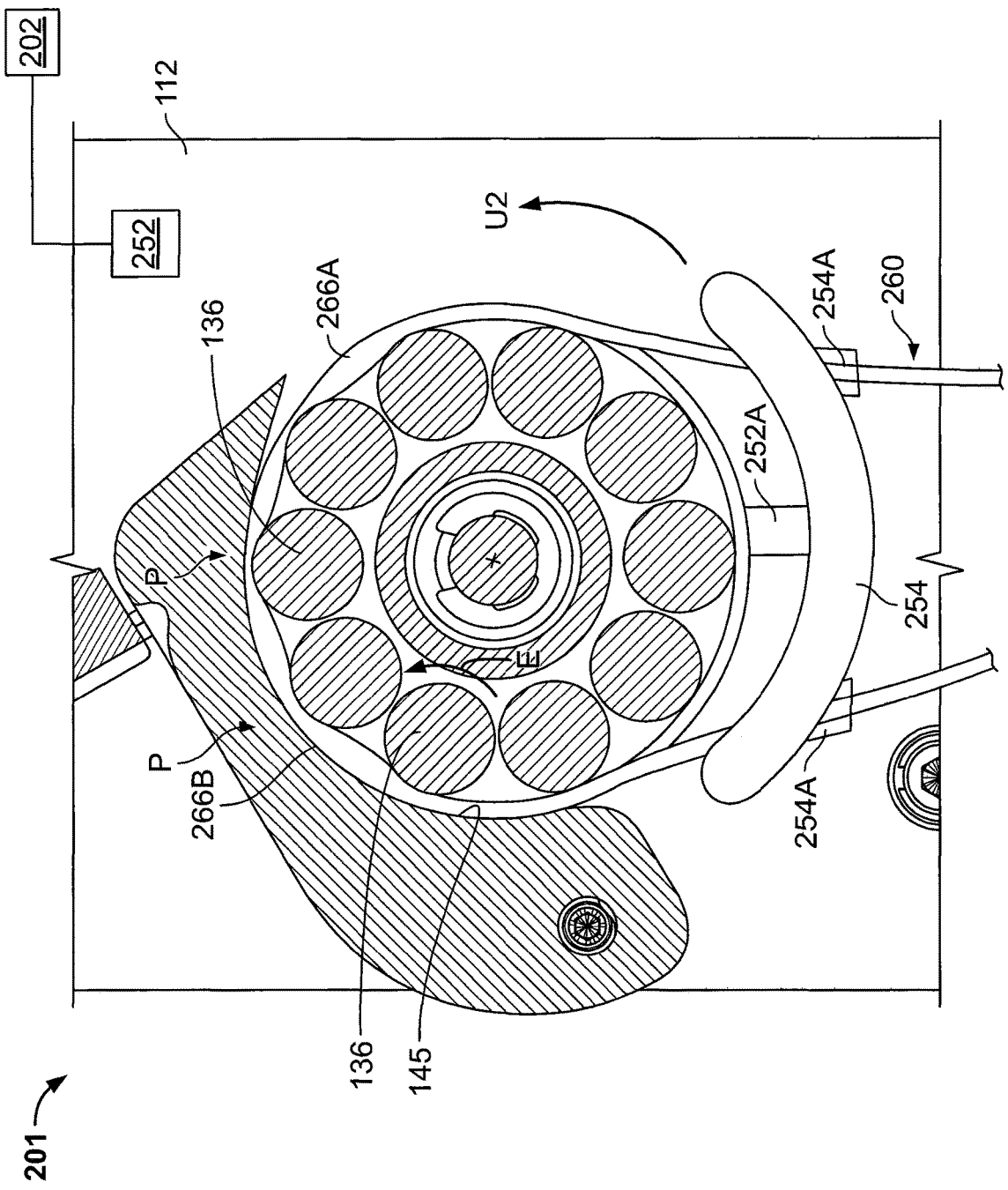
FIG. 9 is a fragmentary, cross-sectional view of the fluid management system of FIG. 8 with the rotator mechanism thereof in a second position.

With reference to FIGS. 8 and 9, a fluid management system 201 according to further embodiments of the technology is shown therein. The fluid management system 201 may be used in place of the fluid management system 101 and is constructed in the same manner as the fluid management system 101, except as follows. In the description below, like numbers are used to designate components and features that are the same as those bearing those numbers in FIGS. 1-7C. The fluid management system 201 includes one or more flexible tubes 260 corresponding to the flexible tube 160 and which may be constructed in the same manner and of the same materials as described herein for the tube 160.

The system 201 includes a translator mechanism 250 instead of the rotator mechanism 150. The translator mechanism 250 includes a tube holder 254 and a displacement actuator 252. In the illustrated embodiment, the displacement actuator 252 is operatively connected to the tube holder 254 by a linkage including a swing arm 252A.

The inlet section 262 and the outlet section 264 of the tube 260 are secured to the tube holder 254 at spaced apart locations by tube stops 254A, for example. The tube holder 254 is movably mounted on the base 112 such that the tube holder 254 can slide along a constrained arcuate path as indicated by opposed direction arrows U1, U2. According to some embodiments, the arc of the tube holder travel path is substantially centered at the hub rotation axis B-B.

The displacement actuator 252 is connected to the tube holder 254 and operable to force the tube holder 254 to slide along the arcuate path through a prescribed displacement or stroke distance. The displacement actuator 252 may be a motor such as an electric motor (e.g., a stepper motor).

With reference to FIG. 8, the flexible tube 260 has two consecutive intermediate or active sections 266A and 266B. Initially, the tube holder 254 may be disposed at a first position wherein the tube holder 254 is at the rightward end of its path. The tube 260 is disposed in a first axial position along the tube lengthwise axis L-L relative to the contact wall 145. In this position, the tube section 266A is in the compressing region P of the pump assembly 110 where the tube 260 is compressed for pumping. The tube section 266B remains upstream of the compressing region P. A controller 202 rotates the rotor assembly 130 as described above to compress the tube section 266A between the rollers 136 and the contact wall 145 and thereby effect positive displacement pumping of the fluid 5 through the tube section 266.

Thereafter, the controller 202 operates the displacement actuator 252 to slide or pivot the tube holder in the direction U1 (FIG. 8). The tube holder 254 pulls or slides the tube sections 266A, 266B downstream. In this manner, the tube 260 is displaced into a second axial position (different from the first axial position) along the tube lengthwise axis L-L relative to the contact wall 145, as shown in FIG. 9. In the second axial position, the tube section 266B is in the compressing region P (extending from location P1 to location P2) of the pump assembly 110 where the tube 260 is compressed for pumping. The tube section 266A is relocated downstream of the compressing region P. The controller 102 rotates the rotor assembly 130 as described above to compress the tube section 266B between the rollers 136 and the contact wall 145 and thereby effect positive displacement pumping of the fluid 5 through the tube section 266B.

As a result, the locations of the bends (i.e., corresponding to bends 172) on the tube 260 are relocated axially along the length of the tube 260. In this manner, the small or sharp radius bends are more widely distributed across the length of the tube, thereby reducing the amount of repetitive deformation experienced by any one location for a given duration of pumping.

The tube 260 may be axially advanced during or between pumping cycles. In some embodiments, the translation from the first axial position to the second axial position is executed while the pump assembly 110 is pumping (i.e., while the rotor assembly 130 is being rotated by the motor 114A). In some embodiments, the translation from the first axial position to the second axial position is executed between pumping sessions (e.g., while the rotor assembly 130 is not being rotated by the motor 114A).

The controller 202 may thereafter operate the actuator 252 to drive the tube holder 254 in a second direction U2 (FIG. 9) to return the tube holder 254 to the first position (FIG. 8), for example. In this way, the tube section 266A is returned to the compressing region P, where it is compressed and released by the rollers 136 to effect peristaltic pumping. The tube holder 254 may be moved back and forth in this manner multiple times during or between pumping sessions.

In some embodiments, the controller 202 automatically and programmatically operates the motor 114A and the actuator 252 to execute the actions, processes and steps discussed above. In other embodiments or modes, the translator mechanism is manually operated.

Figure 10:
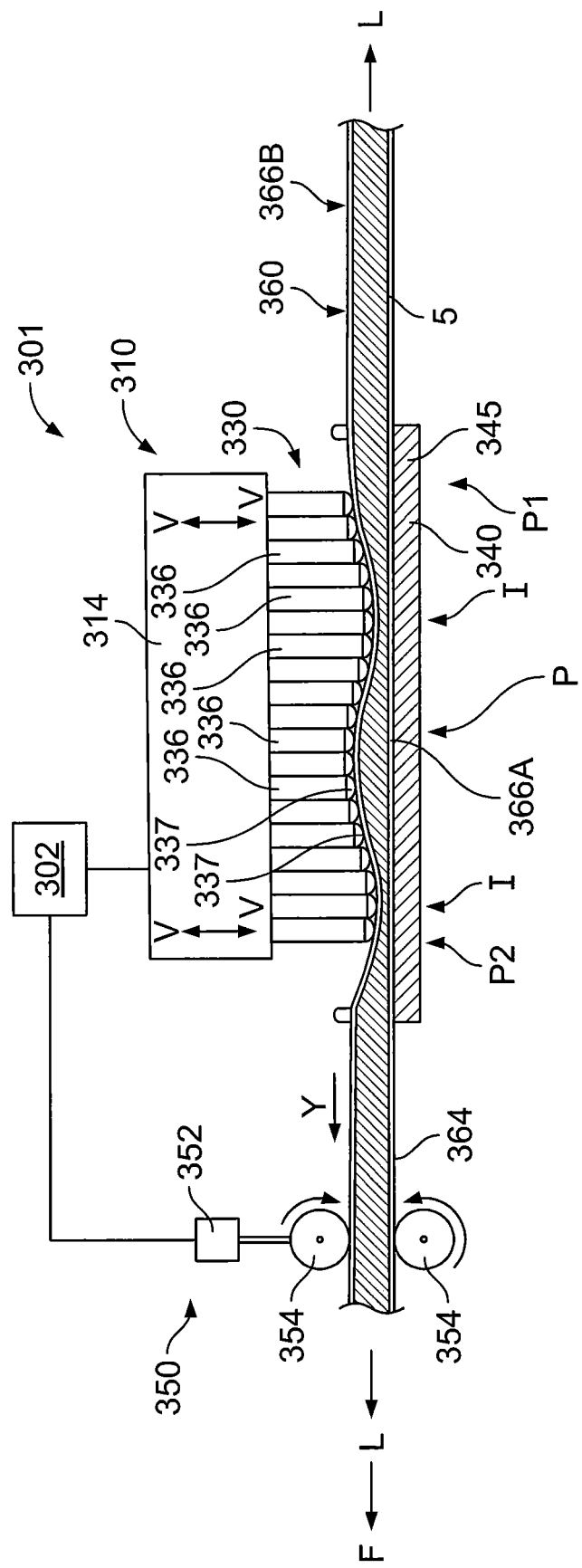
FIG. 10 is a fragmentary side view of a fluid management system according to further embodiments of the technology including a linear peristaltic pump mechanism and a translator mechanism.

With reference to FIG. 10, a fluid management system 301 according to further embodiments of the technology is shown therein. The fluid management system 301 may be used in place of the fluid management system 101 and is constructed in the same manner as the fluid management system 101 except as follows. The fluid management system 301 includes a flexible tube 360 corresponding to the flexible tube 160 and which may be constructed in the same manner and of the same materials as described herein for the tube 160.

The fluid management system 301 includes a pump assembly 310. The pump assembly 310 is a linear peristaltic pump. The pump assembly 310 includes an anvil or substrate 340, a plurality or set 330 of compression members, effectors or fingers 336, and a compression member drive mechanism 314. Each of the compression members 336 has a distal end surface 337. The substrate 340 has a contact surface or wall 345 opposing the end surfaces 337. The compression member drive mechanism 314 includes an actuator operable to forcibly and controllably reciprocate (translate) the compression members 336 toward and away from the contact wall 345 along respective axes V orthogonal to the contact wall 345. The flexible tube 360 is routed between the contact wall 345 and the opposing end surfaces 337 along the length of the compression member set 330.

The end surface 337 and the contact wall 345 define a compressing region P therebetween. The compressing region P extends axially from the location P1 of the first compression element 336 to the location P2 of the last compression element 336.

In use, a controller 302 operates the compression member drive mechanism 314 to sequentially force adjacent compression members 336 toward the contact wall 345 to squeeze or pinch the tube 360 along the compressing region P. The compression members 336 thereby sequentially locally radially compress or pinch the tube 360 against the contact wall 345 at moving pinch locations I. At each pinch location I, the tube 360 is collapsed, deformed or flattened to form substantially flat or elongate side sections and bends corresponding to the side sections 170 and bends 172. The compression members 336 thereby operate as pressing elements while the contact wall 345 serves as an occlusion bed. In some embodiments, the compression members 336 fully occlude the through passage of the tube 360 at the pinched locations. In some embodiments, the compression members 336 do not fully occlude the through passage 369.

As the compression members 336 are sequentially reciprocated, the pinched portions of the tube 360 move or translate progressively down the length of the tube 360 toward the outlet section 364. In this manner, the fluid in the through passage of the tube 360 is squeezed or pushed ahead of the depressing compression member 336 in a fluid flow or displacement direction F through the through passage along the longitudinal axis L-L of the tube 360. The pump mechanism 310 thereby operates as a positive displacement pump. After each compression member 336 is drawn away from the contact wall 345, the tube 360 will resiliently or elastically return (restitution) to its original relaxed or radially expanded state, thereby inducing or drawing more fluid 5 from a supply into through bore of the tube 360. This additional fluid 5 is pushed through the through bore by the next wave of depressions by the compression members 336. The fluid 5 exits the pump mechanism 310 through the tube outlet section 364.

The pump assembly 310 further includes a translator mechanism 350. The translator mechanism 350 includes a displacement actuator 352 (e.g., an electric motor) and a pair of opposed rollers 354 defining a nip. One or both of the rollers 354 is/are driven by the actuator 352. The tube 360 is captured between the rollers 354 such that when the rollers 354 are driven by the actuator 352 the tube 360 is thereby pulled in an upstream direction Y.

In use, the flexible tube 360 has two consecutive sections 366A and 366B. Initially, the tube 360 is disposed in a first axial position along the tube lengthwise axis L-L relative to the contact wall 345. In this position, the tube section 366A is in the active or compressing region P of the pump assembly 310 where the tube 360 is compressed for pumping. The tube section 366B remains upstream of the compressing region P. The controller 302 operates the compression member drive mechanism 314 as described above to compress the tube section 366A between the compression members 336 and the contact wall 345 and thereby effect positive displacement pumping of the fluid 5 through the tube section 366A.

Thereafter, the controller 302 operates the displacement actuator 352 to drive the rollers 354. The rollers 354 pull the tube sections 366A, 366B downstream. In this manner, the tube 360 is displaced into a second axial position (different from the first axial position) along the tube lengthwise axis L-L relative to the contact wall 345. In the second axial position, the tube section 366B is in the compressing region P of the pump assembly 310 where the tube 360 is compressed for pumping. The tube section 366A is relocated downstream of the compressing region P. The controller 302 operates the compression member drive mechanism 314 as described above to compress the tube section 366B between the compression members 336 and the contact wall 345 and thereby effect positive displacement pumping of the fluid 5 through the tube section 366B. As a result, the locations of the bends (corresponding to the bends 172) on the tube 360 are relocated axially along the length of the tube 360. In this manner, the small or sharp radius bends are more widely distributed across the length of the tube, thereby reducing the amount of repetitive deformation experienced by any one location for a given duration of pumping.

The tube 360 may be axially advanced during or between pumping cycles. In some embodiments, the translation from the first axial position to the second axial position is executed while the pump assembly 310 is pumping (i.e., while the compression members 336 are being reciprocated by the drive mechanism 314). In some embodiments, the translation from the first axial position to the second axial position is executed between pumping sessions (e.g., while the compression members 336 are not being reciprocated by the drive mechanism 314).

In some embodiments, the controller 302 automatically and programmatically operates the drive mechanism 314 and the translator mechanism 350 to execute the actions, processes and steps discussed above. In other embodiments or modes, the translator mechanism is manually operated.

Figure 11:
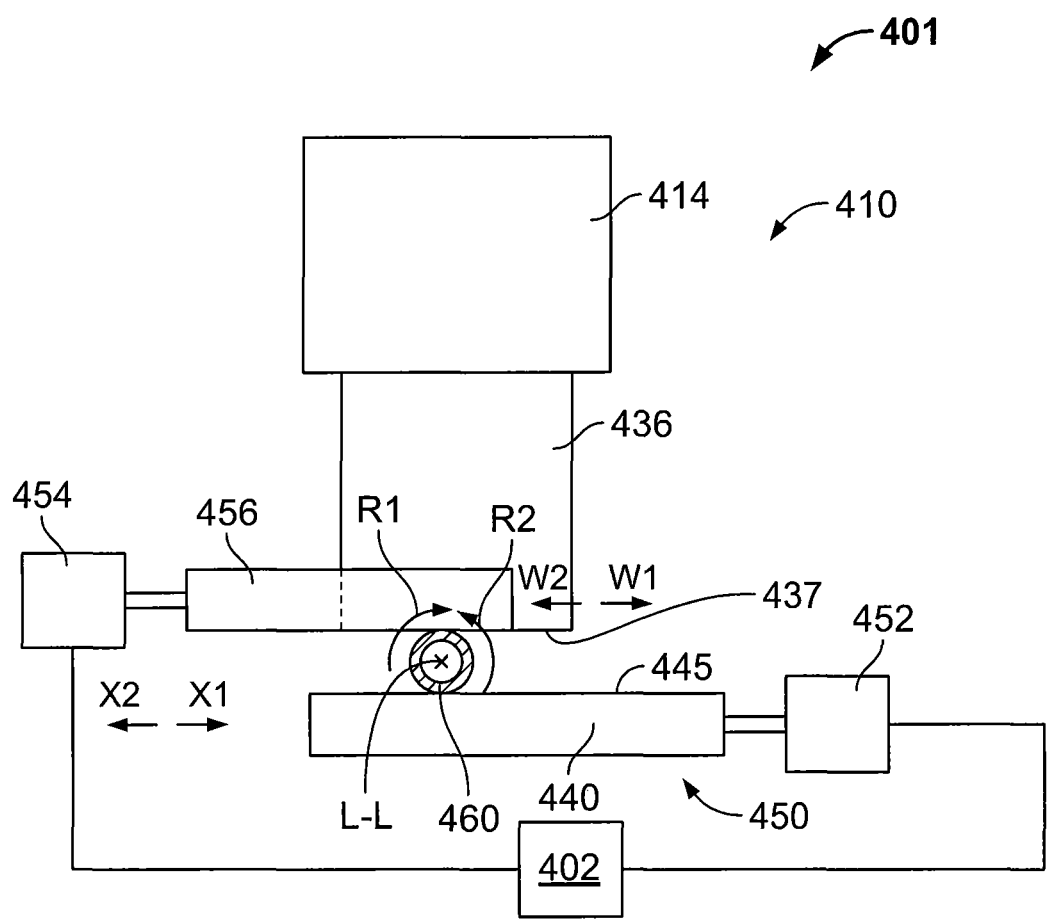
FIG. 11 is a fragmentary end view of a fluid management system according to further embodiments of the technology including a linear peristaltic pump mechanism and a rotator mechanism.

With reference to FIG. 11, a fluid management system 401 according to further embodiments of the technology is shown therein. The fluid management system 401 may be used in place of the fluid management system 301 and is constructed in the manner as the fluid management system 301 except as follows. The fluid management system 401 includes a flexible tube 460 corresponding to the flexible tube 160 and which may be constructed in the same manner and of the same materials as described herein for the tube 160. The fluid management system 401 includes a linear peristaltic pump mechanism 410 constructed and operative in the same manner as the pump mechanism 310. The tube 460 is captured in a compressing region P between the ends 437 of the compression members 436 and the contact wall 445 corresponding to the compressing region P of FIG. 10.

The system 401 includes a rotator mechanism 450 instead of a translator mechanism 150. The rotator mechanism 450 includes a displacement actuator 452 coupled to the substrate 440 by an output shaft. The rotator mechanism also includes a second displacement actuator 454 coupled to an engagement member 456. The controller 402 is operable to operate the actuator 352 to drive the substrate 440, and thereby the contact wall 445, in opposed directions W1 and W2 along an axis transverse or perpendicular to the tube lengthwise axis L-L relative to the compression members 436. The controller 402 is also operative to operate the actuator 454 to drive the engagement member 456 in opposed directions X1 and X2 along an axis transverse or perpendicular to the tube lengthwise axis L-L and substantially parallel to the directions W1, W2. The tube 460 is captured between the engagement member 356 and the contact wall 445. In use, the controller 402 operates the actuators 452, 454 to displace the substrate 440 and the engagement member 456 in opposite directions (i.e., directions W1 and X2 and, alternatively, directions W2 and X1). When the members 440, 456 are driven in directions W1 and X2, the tube 460 is thereby forcibly rotated in a first rotation direction R1 about the tube lengthwise axis L-L. When the members 440, 456 are driven in directions W2 and X1, the tube 460 is thereby forcibly rotated in an opposing second rotation direction R2 about the tube lengthwise axis L-L In use, the pump mechanism 410 is used to pump the fluid through the tube 460 as described above with regard to the pump mechanism 310. The pump mechanism 410 includes a drive mechanism 414 and a plurality of compression members 436 corresponding to the drive mechanism 314 and the compression members 436.

Additionally, in use, the rotator mechanism 450 forcibly rotates of the tube 460 about its lengthwise axis L-L relative to the compression members 436 and the contact wall 445 to thereby change the angular orientation of the tube 460 about the lengthwise axis L-L. More particularly, with the tube section 460 in the first rotational position with a first angular orientation about the axis L-L, the controller 402 operates the rotator mechanism 450 to rotate the tube 460 in the first rotation direction R1 into a second rotational position wherein the tube 460 has a second angular orientation about the axis L-L different from the first angular orientation. The movement of the contact surface 445 and the engagement member 456 forces the tube 460 to rotate in the first direction R1.

According to some embodiments, the angular displacement between the first angular orientation and the second angular orientation is at least 20 degrees, in some embodiments, is in the range of from about 20 to 160 degrees and, in some embodiments, is substantially 90 degrees.

In accordance with some embodiments, with the tube 460 in the second rotational position, the controller 402 operates the rotator mechanism 450 to rotate the tube 460 in the second rotation direction R2 into a third rotational position. The movement of the contact surface 445 and the engagement member 456 forces the tube section 460 to rotate in the second direction R2.

In some embodiments, the third rotational position is the same as the first rotational position and the angular orientation of the tube 460 in the third rotational position is substantially the same as the first angular orientation. However, in other embodiments, the angular orientation of the tube section 460 in the third rotational position is greater or less than the first angular orientation. The tube 460 is captured in a compressing region P between the ends 437 of the compression members 436 and the contact wall 445 corresponding to the compressing region P of FIG. 10.

The foregoing process may be executed only once or multiple times with the same linear section of the tube 460. If executed multiple times, the process may be executed continuously or periodically. The tube 460 may be rotated during or between pumping cycles. In some embodiments, the rotation from the first rotation position to the second rotational position is executed while the pump mechanism 410 is pumping. In some embodiments, the rotation from the second rotation position to the third rotational position is executed while the pump mechanism 410 is pumping. In some embodiments, the both rotations are executed while the pump mechanism 410 is pumping.

In some embodiments, the controller 402 automatically and programmatically operates the pump mechanism 410 and the rotator mechanism 450 to execute the actions, processes and steps discussed above. In other embodiments or modes, the rotator mechanism 450 is manually operated.

Other suitable mechanisms may be employed to induce rotation in the tube 460. For example, in further embodiments, the translator mechanism 450 may include an actuator to move the compression members 436 laterally in place of or in addition to the displacement actuator 454 and the engagement member 456.

In further embodiments, the system 401 may further include a translator mechanism corresponding to the translator mechanism 350. In this case, the tube may be both translated and rotated relative to the compressing region P to distribute deformation of the tube.

Figure 12:
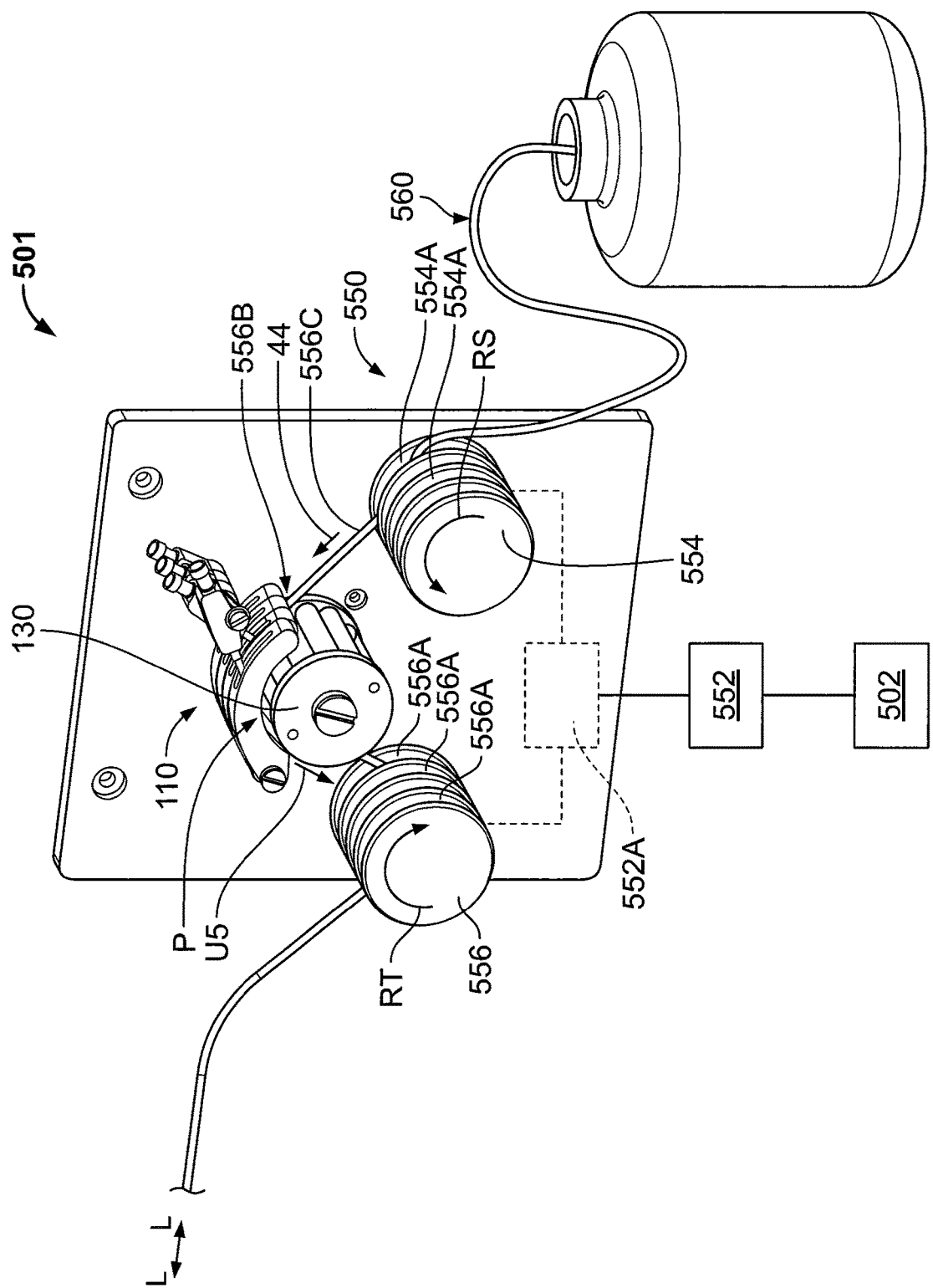
FIG. 12 is a fragmentary, perspective view of a fluid management system according to further embodiments of the technology.

With reference to FIG. 12, a fluid management system 501 according to further embodiments of the technology is shown therein. The fluid management system 501 may be used in place of the fluid management system 201 and is constructed in the same manner as the fluid management system 201, except as follows. In the description below, like numbers are used to designate components and features that are the same as those bearing those numbers in FIGS. 1-9. The fluid management system 501 includes one or more flexible tubes 560 corresponding to the flexible tube 260 and which may be constructed in the same manner and of the same materials as described herein for the tube 160.

The system 501 includes a translator mechanism 550 instead of the translator mechanism 250. The translator mechanism 550 includes a displacement actuator 552, a supply spool 554, a take up spool 556 and an actuator linkage 552A.

The actuator 552 may be a motor such as an electric motor (e.g., a stepper motor). One or both of the spools 554, 556 are driven by the actuator 552 through the linkage 552A so that the rotations of the spools 554, 556 are synchronized with one another. In other embodiments, the spools 554, 556 may be driven by different respective actuators that are otherwise synchronized.

The flexible tube 560 has a leading or downstream section 566A, an intermediate or active section 566B, and a trailing or upstream section 566C. The tube 560 is disposed in a first axial position along the tube lengthwise axis L-L relative to the contact wall 145 (FIG. 6). In this position, the tube section 566B is in the compressing region P (FIG. 3) of the pump assembly 110 where the tube 560 is compressed for pumping. The tube section 566C remains upstream of the compressing region P. A controller 502 rotates the rotor assembly 130 as described above to compress the tube section 566B between the rollers 136 and the contact wall 145 and thereby effect positive displacement pumping of the fluid 5 (FIG. 6) through the tube section 566B.

Thereafter, the controller 502 operates the displacement actuator 552 to rotate the spool 554 in the direction RS and to rotate the spool 556 in the direction RT. The spool 554 thereby pays out a length of the tube 560 (in direction U4) and the spool 556 draws a length of the tube 560 onto the spool 556 (in direction U5) and pulls or slides the tube 560 downstream relative to the compressing region P. In this manner, the tube 560 is displaced into a second axial position (different from the first axial position) along the tube lengthwise axis L-L relative to the contact wall 145. In the second axial position, the formerly upstream section 566C of the tube 560 is in the compressing region P of the pump assembly 110 where the tube 560 is compressed for pumping. The tube section 556B is relocated downstream of the compressing region P. The controller 102 rotates the rotor assembly 130 as described above to compress the tube section 556C between the rollers 136 and the contact wall 145 and thereby effect positive displacement pumping of the fluid 5 through the tube section 556C.

As a result, the locations of the bends (i.e., corresponding to bends 172) on the tube 560 are relocated axially along the length of the tube 560. In this manner, the small or sharp radius bends are more widely distributed across the length of the tube, thereby reducing the amount of repetitive deformation experienced by any one location for a given duration of pumping.

The tube 560 may be axially advanced during or between pumping cycles. In some embodiments, the translation from the first axial position to the second axial position is executed while the pump assembly 110 is pumping (i.e., while the rotor assembly 130 is being rotated by the motor 114A). In some embodiments, the translation from the first axial position to the second axial position is executed between pumping sessions (e.g., while the rotor assembly 130 is not being rotated by the motor 114A).

The controller 502 may thereafter operate the actuator 552 to drive the spools 554, 556 in the same manner as discussed above to further axially advance the tube 560 through the compressing region P. The tube 560 may be advanced in this manner continuously or intermittently multiple times during or between pumping sessions.

In some embodiments, the controller 502 automatically and programmatically operates the motor 114A (FIG. 2) and the actuator 552 to execute the actions, processes and steps discussed above. In other embodiments or modes, the translator mechanism 550 is manually operated.

In some embodiments and as illustrated in FIG. 12, for example, each spool includes multiple tube receiving sections or circumferential grooves 554A, 556A (as shown, four each). Each groove 554A, 556A receives a respective one of a plurality of tubes 560 (only one shown) that are routed through the pump assembly 120. In this manner, the fluid management system 501 can pump fluid through two or more tubes 560 as described above, and each of the tubes 560 can be axially advanced by the translator mechanism 550.

Figure 13:
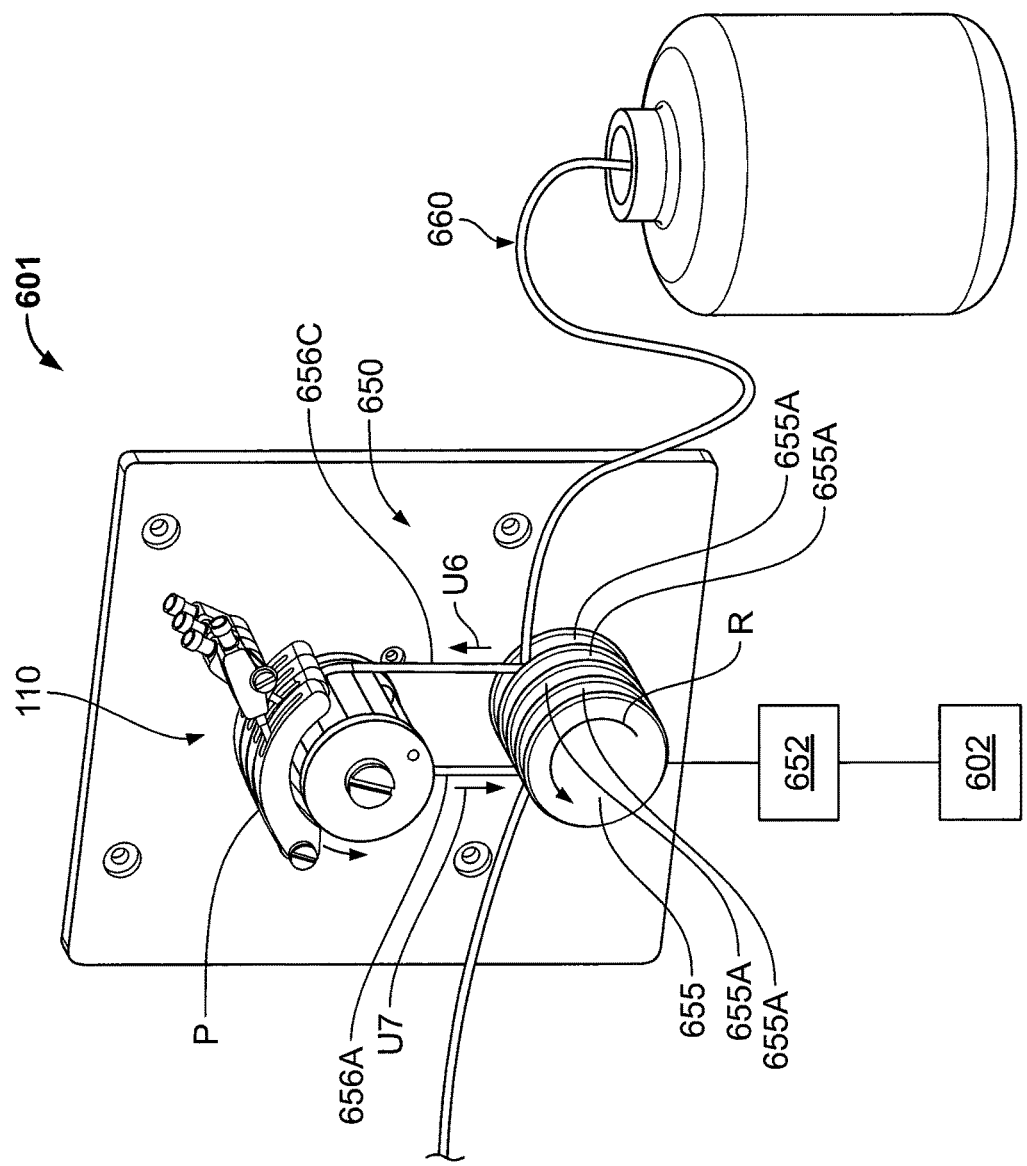
FIG. 13 is a fragmentary, perspective view of a fluid management system according to further embodiments of the technology.

With reference to FIG. 13, a fluid management system 601 according to further embodiments of the technology is shown therein. The fluid management system 601 may be used in place of the fluid management system 501 and is constructed in the same manner as the fluid management system 501, except as follows. In the description below, like numbers are used to designate components and features that are the same as those bearing those numbers in FIGS. 1-9. The fluid management system 601 includes one or more flexible tubes 660 corresponding to the flexible tube 560 and which may be constructed in the same manner and of the same materials as described herein for the tube 160.

The system 601 includes a translator mechanism 650 instead of the translator mechanism 550. The translator mechanism 650 includes a displacement actuator 652, and a single spool 655 that operates as both a supply spool (corresponding to the supply spool 554) and a take up spool (corresponding to the take up spool 556).

In use, the controller 602 operates the displacement actuator 652 to rotate the spool 655 in the direction R. The spool 655 thereby pays out a length 656C of the tube 660 in a direction U6 from the spool 655 toward the compressing region P. The spool 655 also thereby takes up a length 656A of the tube 660 in a direction U7 onto the spool 655 away the compressing region P. In this manner, the tube 660 is displaced into a second axial position (different from the first axial position) along the tube lengthwise axis L-L relative to the contact wall 145. In the second axial position, the formerly upstream section of the tube 660 is in the compressing region P (extending from location P1 to location P2) of the pump assembly 110 where the tube 660 is compressed for pumping. The tube section that was previously in the compressing region P is relocated downstream of the compressing region P. The controller 102 rotates the rotor assembly 130 as described above to compress the tube section between the rollers 136 and the contact wall 145 and thereby effect positive displacement pumping of the fluid 5 through the tube section.

The tube 660 may be axially advanced as discussed above with regard to the system 501.

In some embodiments and as illustrated in FIG. 13, for example, the spool 655 includes multiple tube receiving sections or circumferential grooves 655A (as shown, four). One groove 655A receives the upstream tube section 656C of the tube 660 and another groove 655A receives the downstream tube section 656A of the tube 660. The other two grooves 655A can receive the upstream and downstream sections of another tube 660 that is routed through the pump assembly 110. In this manner, the fluid management system 601 can pump fluid through two tubes 660 as described above, and each of the tubes 660 can be axially advanced by the translator mechanism 650.

In some embodiments, an extended or extra length of the tube may be stored on the spool. For example, multiple turns of the tube may be helically or spirally wound or wrapped around the spool.

While the tube displacement mechanisms (e.g., mechanisms 150, 250, 350, 450, 550, 650) have been described herein having their own dedicated actuators, in some embodiments they may instead be powered, actuated or driven by shared actuators. For example, the tube displacement mechanisms may be driven (e.g., through a linkage) by the actuators that drive the motor rotation or compression member reciprocation. In some embodiments, the tube displacement mechanisms are manually driven (i.e., human-powered).

Herein, where it has been expressed that the flexible tube can be or is displaced (e.g., rotated or translated) relative to the compression region P and the contact surfaces and contact walls, it will be understood that such displacement may be effected by moving the tube and/or the other components of the pump such that relative displacement between the tube and such other components is achieved. For example, the tube may be held in place (relative to free space) while the compressing region and contact wall are rotated or translated in order to displace the tube relative to the compressing region P and the contact wall.

In further embodiments, in addition to or in place of the rotator mechanism 150, the rollers 136 may be shaped such that they cause or induce rotation in the tube section 166 about the axis L-L as the rotator 130 is rotated.

In further embodiments, in addition to or in place of the translator mechanism 250, the rollers 236 of the system 201 can be shaped to cause the tube section 266A to translate or advance axially through the compressing region P as the motor 130 is rotated.

In some embodiments, the tube section 166 or 460 is rotated at a rate in the range of from about 0.5 to 100 degrees/minute.

In some embodiments, the tube section 166 or 460 is rotated at a rate in the range of from about 0.001 to 0.1 degrees per one hundred cycles of compression and relaxation of the tube section 166, 460.

In some embodiments, the tube 260, 360, 560 or 660 is axially advanced through the compressing region P at a rate of from about 1 to 100 cm/minute.

In some embodiments, the tube 260, 360, 560 or 660 is axially advanced through the compressing region P at a rate of from about 0.00002 to 0.002 centimeters per one hundred cycles of compression and relaxation of the tube section 266A, 266B, 366A, 366B, 566B in the compressing region P.

A translator mechanism including a spool or spools corresponding to the translator mechanism 550 or 650 may also be used to axially advance the tube 360 through the pump mechanism 310 (FIG. 10).

Pump mechanisms, tube displacement mechanisms and methods as disclosed herein can reduce the frequency with which the flexible tube must or should be replaced in the pump mechanism. The time, cost and inconvenience of removing the flexible tube and installing a new flexible tube can thus be reduced. This may be particularly advantageous in the case of flexible tubes that must be prepared (for example, cleaned out) before first use.

According to some embodiments, the pump mechanisms (e.g., pump mechanism 120) as disclosed herein are used to pump fluid to a spectrometer or other precision fluid analysis apparatus. In some embodiments, the pump mechanisms are used as medical infusion pumps. The foregoing benefits of the tube displacement methods and mechanisms may be particularly beneficial when used to feed the fluid to such apparatus. The more consistent and stable pumping performance afforded by the tube displacement methods and mechanisms can enable better sensitivity in the data collected and more reliable and accurate analytic results Many alterations and modifications may be made by those having ordinary skill in the art, given the benefit of present disclosure, without departing from the spirit and scope of the technology. Therefore, it must be understood that the illustrated embodiments have been set forth only for the purposes of example, and that it should not be taken as limiting the technology as defined by the following claims. The following claims, therefore, are to be read to include not only the combination of elements which are literally set forth but all equivalent elements for performing substantially the same function in substantially the same way to obtain substantially the same result. The claims are thus to be understood to include what is specifically illustrated and described above, what is conceptually equivalent, and also what incorporates the essential idea of the technology.

What is claimed:

1. A method for pumping a fluid, the method comprising:
   providing a peristaltic pump including:
   a contact wall;
   a rotor including a compression element, wherein:
      the rotor is rotatable relative to the contact wall about a rotation axis;
      the compression element opposes the contact wall; and
      the contact wall and the compression element define a compressing region therebetween; and
   a flexible tube interposed between the contact wall and the compression element in the compressing region, the flexible tube having a tube lengthwise axis and inner and outer opposed wall surfaces, the inner wall surface defining a through passage to receive the fluid;
   wherein the flexible tube is displaceable relative to the compressing region between a first position and a second position different from the first position;
   with the flexible tube in the first position, compressing the flexible tube between the compression element and the contact wall to thereby force the fluid through the through passage; thereafter
   displacing the flexible tube into the second position from the first position, including axially displacing the compression element relative to the contact wall along a compression member displacement axis substantially parallel to the rotation axis and/or axially displacing the contact wall relative to the compression element along a contact wall displacement axis substantially parallel to the rotation axis; and thereafter
   with the flexible tube in the second position, compressing the flexible tube between the compression element and the contact wall to thereby force the fluid through the through passage.

2. The method of claim 1 wherein:
   the first position is a first rotational position having a first angular orientation about the tube lengthwise axis and the second position is a second rotational position having a second angular orientation about the tube lengthwise axis different from the first angular orientation;
   the flexible tube is rotatable about the tube lengthwise axis relative to the compressing region between the first rotational position and the second rotational position; and
   the step of displacing the flexible tube into the second position from the first position includes rotating the flexible tube into the second rotational position from the first rotational position.

3. The method of claim 2 wherein:
   rotating the flexible tube about the tube lengthwise axis into the second rotational position includes rotating the flexible tube in a first rotation direction; and
   the method further includes, following the step of compressing the flexible tube between the compression element and the contact wall with the flexible tube in the second rotational position:
      rotating the flexible tube about the tube lengthwise axis in a second rotation direction opposite the first rotation direction into a third rotational position, including axially displacing the compression element relative to the contact wall along the compression element displacement axis and/or axially displacing the contact wall relative to the compression element along the contact wall displacement axis; and thereafter
      with the flexible tube in the third rotational position, compressing the flexible tube between the compression element and the contact wall to thereby force the fluid through the through passage.

4. The method of claim 2 including compressing the flexible tube between the compression element and the contact wall to thereby force the fluid through the through passage during the step of rotating the flexible tube about the tube lengthwise axis into the second rotational position from the first rotational position.

5. The method of claim 2 wherein the second angular orientation is at least 20 degrees from the first angular orientation.

6. The method of claim 2 wherein the second angular orientation is in the range from 20 to 160 degrees from the first angular orientation.

7. The method of claim 2 wherein the step of rotating the flexible tube about the tube lengthwise axis into the second rotational position from the first rotational position includes rotating the flexible tube using a rotator mechanism to axially displace the compression element relative to the contact wall along the compression element displacement axis and/or axially displace the contact wall relative to the compression element along the contact wall displacement axis.

8. The method of claim 7 wherein the rotator mechanism includes a powered actuator.

9. The method of claim 8 wherein the rotator mechanism includes a controller that programmatically drives the actuator to axially displace the compression element relative to the contact wall along the compression element displacement axis and/or axially displace the contact wall relative to the compression element along the contact wall displacement axis.

10. The method of claim 7 wherein the rotator mechanism moves the compression element and/or the contact wall in a direction transverse to the tube lengthwise axis at a location in the compressing region to thereby rotate the flexible tube about the tube lengthwise axis.

11. The method of claim 10 wherein the rotator mechanism moves the compression element in a first direction transverse to the tube lengthwise axis at the location in the compressing region and moves the contact wall in a second direction opposite the first direction to thereby rotate the flexible tube about the tube lengthwise axis.

12. The method of claim 1 wherein the step of compressing the flexible tube between the compression element and the contact wall with the flexible tube in the second position includes forcing the compression element to travel down a length of the flexible tube while engaging and compressing the flexible tube to thereby push the fluid axially through the through passage.

13. The method of claim 12 wherein the peristaltic pump is a rotary peristaltic pump and the compression element is a compression roller, shoe or wiper.

14. The method of claim 13 wherein:
the rotor includes a carrier and a plurality of circumferentially spaced apart compression rollers, shoes or wipers located on the carrier for rotation therewith about the rotation axis; and
the step of compressing the flexible tube between the compression element and the contact wall with the flexible tube in the second position includes compressing the flexible tube between the contact wall and each of the compression rollers, shoes or wipers.

15. The method of claim 14 wherein the compression elements are rollers mounted on the carrier and each rotatable relative to the carrier about a respective roller axis.

16. The method of claim 1 wherein the step of displacing the flexible tube into the second position from the first position includes axially displacing the compression element relative to the contact wall along the compression element displacement axis in a first direction.

17. The method of claim 16 wherein the step of displacing the flexible tube into the second position from the first position further includes axially displacing the contact wall relative to the compression element along the contact wall displacement axis in a second direction opposite the first direction.

18. The method of claim 1 wherein the step of displacing the flexible tube into the second position from the first position includes axially displacing the contact wall relative to the compression element along the contact wall displacement axis.

19. A method for pumping a fluid, the method comprising:
providing a peristaltic pump including:
a contact wall;
a movable compression element opposing the contact wall, wherein the contact wall and the compression element define a compressing region therebetween; and
a flexible tube interposed between the contact wall and the compression element in the compressing region, the flexible tube having a tube lengthwise axis and inner and outer opposed wall surfaces, the inner wall surface defining a through passage to receive the fluid;
wherein the flexible tube is displaceable relative to the compressing region between a first position and a second position different from the first position;
with the flexible tube in the first position, compressing the flexible tube between the compression element and the contact wall to thereby force the fluid through the through passage; thereafter
displacing the flexible tube into the second position from the first position, including displacing the contact wall axially relative to the compression element element; and thereafter
with the flexible tube in the second position, compressing the flexible tube between the compression element and the contact wall to thereby force the fluid through the through passage.

20. The method of claim 19 including rotating the compression element relative to the contact wall about a rotation axis, and wherein the step of displacing the flexible tube into the second position from the first position includes axially displacing the contact wall relative to the compression element along a contact wall displacement axis substantially parallel to the rotation axis.

21. The method of claim 19 wherein:
the first position is a first rotational position having a first angular orientation about the tube lengthwise axis and the second position is a second rotational position having a second angular orientation about the tube lengthwise axis different from the first angular orientation;
the flexible tube is rotatable about the tube lengthwise axis relative to the compressing region between the first rotational position and the second rotational position;
the step of displacing the flexible tube into the second position from the first position includes rotating the flexible tube into the second rotational position from the first rotational position;
the peristaltic pump includes a rotator mechanism, and the rotator mechanism includes a powered actuator and a controller; and
in the step of rotating the flexible tube about the tube lengthwise axis into the second position from the first position, the controller programmatically drives the powered actuator to displace the contact wall relative to the compression element.

* * * * *

UNITED STATES PATENT AND TRADEMARK OFFICE
CERTIFICATE OF CORRECTION

PATENT NO. : 10,578,097 B2
APPLICATION NO. : 15/481572
DATED : March 3, 2020
INVENTOR(S) : Cheung et al.

Page 1 of 1

It is certified that error appears in the above-identified patent and that said Letters Patent is hereby corrected as shown below:

In the Claims

Column 24, Line 24, Claim 19:
Please correct "compression element element;" to read -- compression element; --

Signed and Sealed this
Seventh Day of July, 2020

Andrei Iancu
*Director of the United States Patent and Trademark Office*